(12) United States Patent
Yen et al.

(10) Patent No.: US 6,593,098 B1
(45) Date of Patent: Jul. 15, 2003

(54) GENES ENCODING PROTEINS INVOLVED IN MITOTIC CHECKPOINT CONTROL AND METHODS OF USE THEREOF

(75) Inventors: Timothy Yen, Havertown, PA (US); Gordon Chan, Cheltenham, PA (US); Sandra Jablonski, Philadelphia, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 09/555,554

(22) PCT Filed: Dec. 1, 1998

(86) PCT No.: PCT/US98/25415
§ 371 (c)(1),
(2), (4) Date: Jun. 1, 2000

(87) PCT Pub. No.: WO99/28334
PCT Pub. Date: Jun. 10, 1999

Related U.S. Application Data

(60) Provisional application No. 60/067,093, filed on Dec. 1, 1997.

(51) Int. Cl.[7] .............................. C12Q 1/48; C12Q 1/68; C12N 15/00; C12N 5/00; C07H 21/04
(52) U.S. Cl. .............................. 435/15; 435/194; 435/6; 435/252.3; 435/320.1; 435/325; 536/23.1; 536/23.2
(58) Field of Search ................ 536/23.2, 23.1; 435/194, 252.3, 320.1, 15; 530/350

(56) References Cited

PUBLICATIONS

Roberts et al. Mol. Cell. Biol., 14, 8282–8291, 1994.*
R. Bruce Nicklas, "How Cells Get the Right Chromosomes", Science, vol. 275, Jan. 31, 1997, pp. 632–637.

Gary J. Gorbsky, "Kinetochores, microtubules and the metaphase checkpoint", Trends in Cell Biology, vol. 5, Apr. 1995, pp. 143–148.

Randall W. King, et al., "How Proteolysis Drivers the Cell Cycle", Science, vol. 274, Dec. 6, 1996, pp. 1652–1659.

M. Andrew Hoyt, "S. cerevisiae Genes Required for Cell Cycle Arrest in Response to Loss of Microtubule Function", Cell, vol. 66, 507–517, Aug. 9, 1991.

Stephen S. Taylor, "Kinetochore Localization of Murine Bub1 Is Required for Normal Mitotic Timing and Checkpoint Response to Spindle Damage", Cell, vol. 89, 727–735, May 30, 1997.

S.A. Jablonski, "The hBUB1 and hBuBR1 kinases sequentially assemble onto kinetochores during prophase with hBUBR1 concentrating at the kinetochore plates in mitosis", Chromosoma (1998) 107: 386–396.

* cited by examiner

*Primary Examiner*—M. Monshipouri
(74) *Attorney, Agent, or Firm*—Dann, Dorfman, Herrell & Skillman, P.C.; Kathleen D. Rigaut

(57) ABSTRACT

Novel human BUB genes and their encoded proteins are provided herein. The kinases encoded by the disclosed BUB1A and BUB1B genes play a pivotal role in mitotic checkpoint control. BUB3 is a substrate of these kinases, BUB genes and their encoded proteins provide valuable therapeutic targets for the design of anti-proliferative agents which inhibit the aberrant cellular proliferation observed in tumor cells.

30 Claims, 16 Drawing Sheets

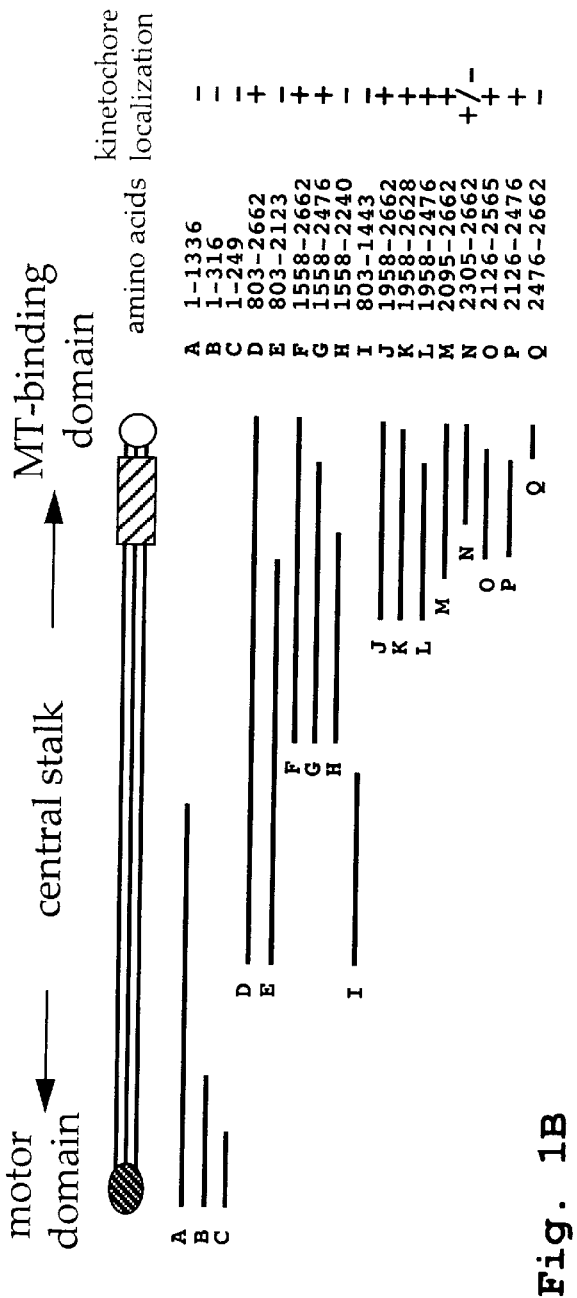
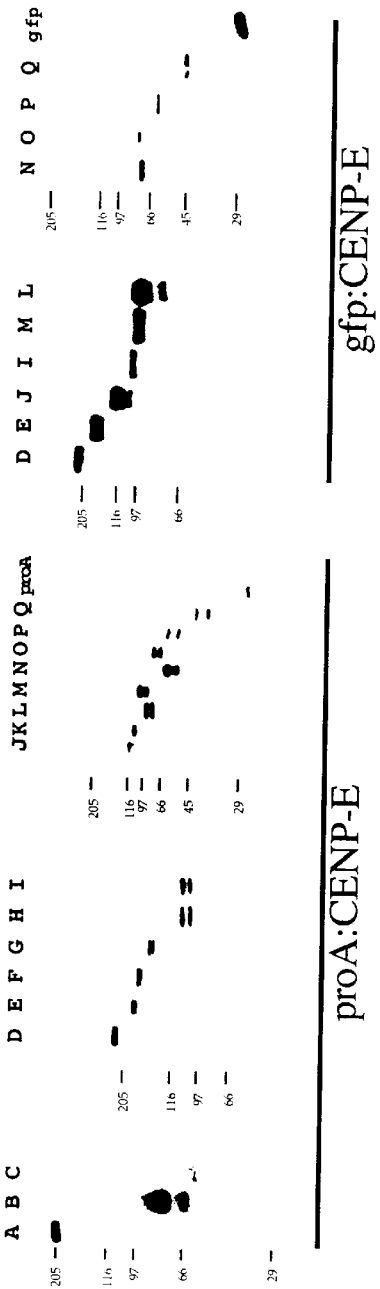
Fig. 1A
Fig. 1B

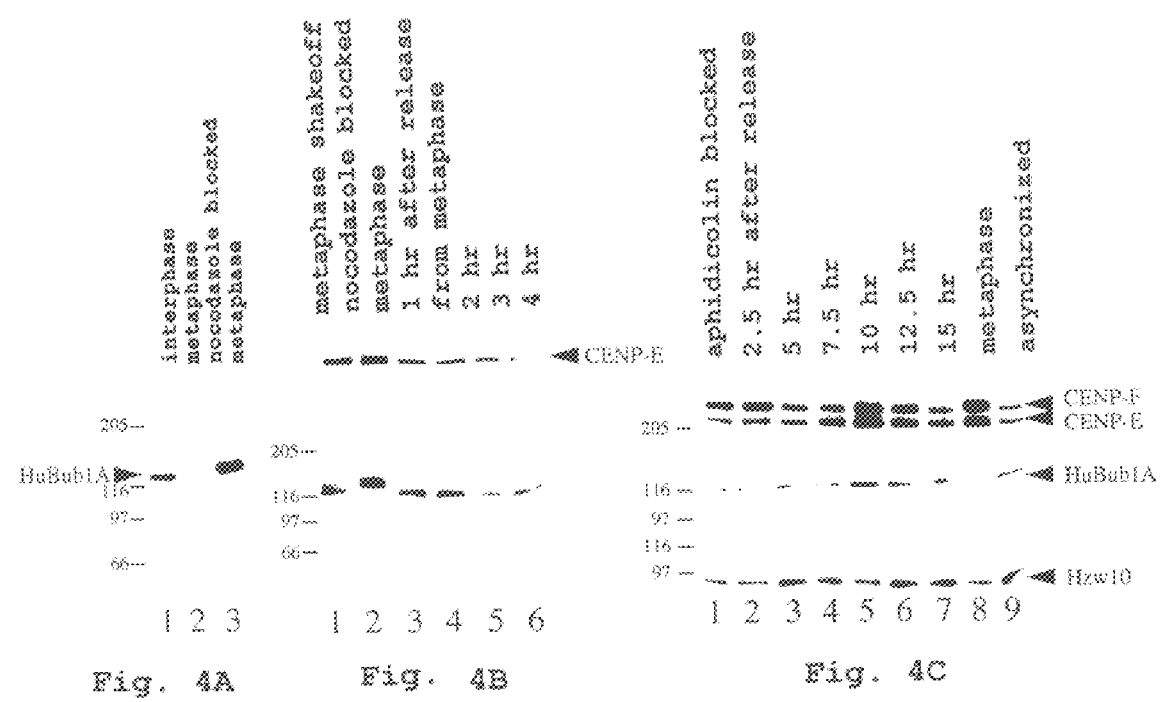

*In vivo* P³² labelling

IgG ▶  ....              ━━
                                                        — 49
        HuBub3 ▶ ━━               ..

HuBub1A      HuBub1B
                ip            ip

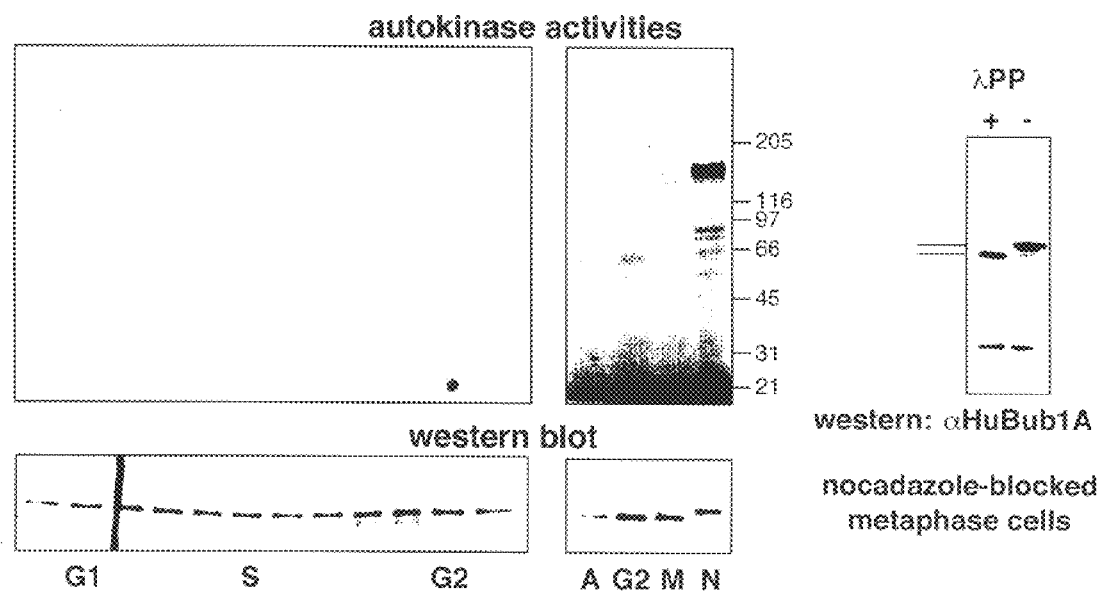
Fig. 10A  HuBub1A exhibits mitosis-specific kinase activity and hyperphosphorylation

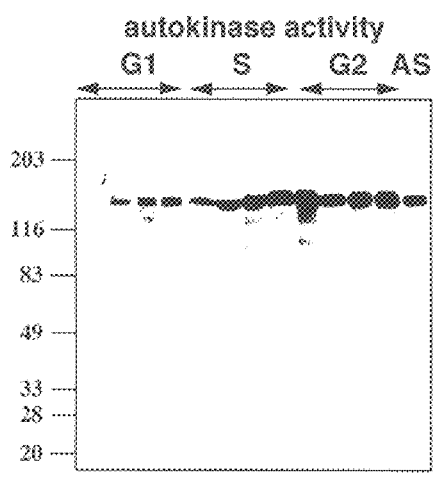
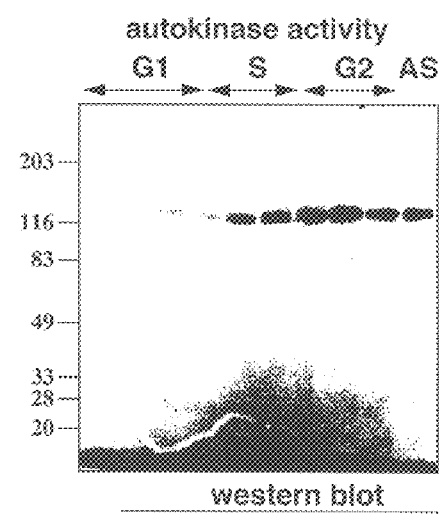
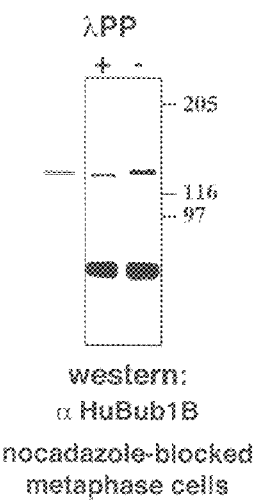
Fig. 10B  HuBub1B-associated kinase profile from elutriated cells

Translation of HuBub1A Sequence

Sequence Range: 1 to 1050

```
              10         20         30         40         50         60         70
      MAAVKKEGGA LSEAMSLEGD EWELSKENVQ PLRQGRIMST LQGALAQESA CNNTLQQQKR AFEYEIRFYT 80         90        100        110        120        130        140
      GNDPLDVWDR YISWTEQNYP QGGKESNMST LLERAVEALQ GEKRYYSDPR FLNLWLKLGR LCNEPLDMYS 150        160        170        180        190        200        210
      YLHNQGIGVS LAQFYISWAE EYEARENFRK ADAIFQEGIQ QKAEPLERLQ SQHRQFQARV SRQTLLALEK 220        230        240        250        260        270        280
      EEEEEVFESS VPQRSTLAEL KSKGKKTARA PIIRVGGALK APSQNRGLQN PFPQQMQNNS RITVFDENAD 290        300        310        320        330        340        350
      EASTAELSKP TVQPWIAPPM PRAKENELQA GPWNTGRSLE HRPRGNTASL IAVPAVLPSF TPYVEETAQQ 360        370        380        390        400        410        420
      PVMTPCKIEP SINHILSTRK PGKEEGDPLQ RVQSHQQASE EKKEKMMYCK EKIYAGVGEF SFEEIRAEVF 430        440        450        460        470        480        490
      RKKLKEQREA ELLTSAEKRA EMQKQIEEME KKLKEIQTTQ QERTGDQQEE TMPTKETTKL QIASESQKIP 500        510        520        530        540        550        560
      GMTLSSSVCQ VNCCARETSL AENIWQEQPH SKGPSVPFSI FDEFLLSEKK NKSPPADPPR VLAQRRPLAV 570        580        590        600        610        620        630
      LKTSESITSN EDVSPDVCDE FTGIEPLSED AIITGFRNVT ICPNPEDTCD FARAARFVST PFHEIMSLKD 640        650        660        670        680        690        700
      LPSDPERLLP EEDLDVKTSE DQQTACGTIY SQTLSIKKLS PIIEDSREAT HSSGFSGSSA SVASTSSIKC 710        720        730        740        750        760        770
      LQIPEKLELT NETSENPTQS PWCSQYRRQL LKSLPELSAS AELCIEDRPM PKLEIEKEIE LGNEDYCIKR 780        790        800        810        820        830        840
      EYLICEDYKL FWVAPRNSAE LTVIKVSSQP VPWDFYINLK LKERLNEDFD HFCSCYQYQD GCIVWHQYIN 850        860        870        880        890        900        910
      CFTLQDLLQH SEYITHEITV LIIYNLLTIV EMLHKAEIVH GDLSPRCLIL RNRIHDPYDC NKNNQALKIV 920        930        940        950        960        970        980
      DFSYSVDLRV QLDVFTLSGF RTVQILEGQK ILANCSSPYQ VDLFGIADLA HLLLFKEHLQ VFWDGSFWKL 990       1000       1010       1020       1030       1040       1050
      SQNISELKDG ELWNKFFVRI LNANDEATVS VLGELAAKMN GVFDTTFQSH LNKALWKVGK LTSPGALLFQ
```

Figure 13

Translation of HuBub1B Sequence

Sequence Range: 1 to 1095

```
         10         20         30         40         50         60         70
MDTPENVLQM LEAHMQSYKG NDPLGEWERY IQWVEENFPE NKEYLITLLE HLMKEFLDKK KYHNDPRFIS 80         90        100        110        120        130        140
YCLKFAEYNS DLHQFFEFLY NHGIGTLSSP LYIAWAGHLE AQGELQHASA VLQRGIQNQA EPREFLQQQY 150        160        170        180        190        200        210
RLFQTRLTET HLPAQARTSE PLHNVQVLNQ MITSKSNPGN NMACISKNQG SELSGVISSA CDKESNMERR 220        230        240        250        260        270        280
VITISKSEYS VHSSLASKVD VEQVVMYCKE KLIRGESEFS FEELRAQKYN QRRKHEQWVN EDRHYMKRKE 290        300        310        320        330        340        350
ANAFEEQLLK QKMDELHKKL HQVVETSHED LPASQERSEV NPARMGPSVG SQQELRAPCL PVTYQQTPVN 360        370        380        390        400        410        420
MEKNPREAPP VVPPLANAIS AALVSPATSQ SIAPPVPLKA QTVTDSMFAV ASKDAGCVNK STHEFKPQSG 430        440        450        460        470        480        490
AEIKEGCETH KVANTSSFHT TPNTSLGMVQ ATPSKVQPSP TVHTKEALGF IMNMFQAPTL PDISDDKDEW 500        510        520        530        540        550        560
QSLDQNEDAF EAQFQKNVRS SGAWGVNKII SSLSSAFHVF EDGNKENYGL PQPKNKPTGA RTFGERSVSR 570        580        590        600        610        620        630
LPSKPKEEVP HAEEFLDDST VWGIRCNKTL APSPKSPGDF TSAAQLASTP FHKLPVESVH ILEDKENVVA 640        650        660        670        680        690        700
KQCTQATLDS CEENMVVPSR DGKFSPIQEK SPKQALSSHM YSASLLRLSQ PAAGGVLTCE AELGVEACRL 710        720        730        740        750        760        770
TDTDAAIAED PPGSAAIAED PPDAIAGLQA EWMQMSSLGT VDAPNFIVGN PWDDKLIFKL LSGLSKPVSS 780        790        800        810        820        830        840
YPNTFEWQCK LPAIKPKTEF QLGSKLVYVH HLLGEGAFAQ VYEATQGDLN DAKNKQKFVL KVQKPANPWE 850        860        870        880        890        900        910
FYIGTQLMER LKPSMQHMFM KFYSAHLFQN GSVLVGELYS YGTLLNAINL YKNTPEKVMP QGLVISFAMR 920        930        940        950        960        970        980
MLYMIEQVHD CEIIHGDIKP DNFILGNGFL EQDDEDDLSA GLALIDLGQS IDMKLFPKGT IFTAKCETSG 990       1000       1010       1020       1030       1040       1050
FQCVEMLSNK PWNYQIDYFG VAATVYCMLF GTYMKVKNEG GECKPEGLFR RLPHLDMWNE FFHVMLNIPD 1060       1070       1080       1090
CHHLPSLDLL RQKLKKVFQQ HYTNKIRALR NRLIVLLLEC KRSRK
```

Figure 14

Translation of HuBub3 Sequence

Sequence Range: 1 to 328

```
         10         20         30         40         50         60         70
MTGSNEFKLN QPPEDGISSV KFSPNTSQFL LVSSWDTSVR LYDVPANSMR LKYQHTGAVL DCAFYDPTHA 80         90        100        110        120        130        140
WSGGLDHQLK MHDLNTDQEN LVGTHDAPIR CVEYCPEVNV MVTGSWDQTV KLWDPRTPCN AGTFSQPEKV 150        160        170        180        190        200        210
YTLSVSGDRL IVGTAGRRVL VWDLRNMGYV QQRRESSLKY QTRCIRAFPN KQGYVLSSIE GRVAVEYLDP 220        230        240        250        260        270        280
SPEVQKKKYA FKCHRLKENN IEQIYPVNAI SFHNIHNTFA TGGSDGFVNI WDPFNKKRLC QFHRYPTSIA 290        300        310        320
SLAFSNDGTT LAIASSYMYE MDDTEHPEDG IFIRQVTDAE TKPKSPCT
```

Figure 15

GENES ENCODING PROTEINS INVOLVED IN MITOTIC CHECKPOINT CONTROL AND METHODS OF USE THEREOF

This application is a 35 U.S.C. §371 application of PCT/US98/25415 entitled "Novel Genes Encoding Proteins Involved in Mitotic Checkpoint Control and Methods of Use Thereof" filed Dec. 1, 1998, which in turn claims priority from U.S. patent application Ser. No. 60/067,093 filed Dec. 1, 1997, the entire disclosure of each being incorporated by reference herein.

Pursuant to 35 U.S.C. S202(c) it is acknowledged that the U.S. Government has certain rights in the invention described herein, which was made in part with funds from the National Institutes of Health, Grant Number, GM44762.

FIELD OF THE INVENTION

This invention relates to agents that may be used to regulate mitosis in eucaryotic cells. Specifically, novel human BUB genes and their encoded proteins are disclosed. These genes and proteins may be used as targets for the development of novel agents that inhibit aberrant cellular proliferation in tumor cells.

BACKGROUND OF THE INVENTION

Several publications are referenced in this application in parentheses in order to more fully describe the state of the art to which this invention pertains. The disclosure of each of these publications is incorporated by reference herein.

The production of two viable and equivalent daughter cells in mitosis requires that events leading to cell division proceed in a carefully ordered fashion. Among other tightly regulated events, replicated sister chromosomes must be properly segregated, one to each daughter cell. For this reason, mitosis cannot be allowed to proceed if the genome has not been fully replicated or if chromosomes are not properly attached to a fully assembled mitotic spindle. Mechanisms required for ensuring the dependency of cell division on completion of such prerequisite steps have been termed mitotic checkpoints (52).

This checkpoint mechanism directly monitors the spatial position of chromosomes within the spindle and applies this information to regulate the activities of proteins that induce chromosome separation and allow the cell to exit mitosis and complete cell division (2, 3, 4). The mitotic checkpoint has sufficient sensitivity to detect the presence of a single unaligned chromosome amidst tens of chromosomes that are aligned (5). Furthermore, this checkpoint will block the cell in mitosis by delaying the onset of anaphase for many hours so that the unaligned chromosome has ample opportunity to establish the spindle connections that allow alignment at the spindle equator. Studies in yeast, insect cells and vertebrate cells show that this mitotic checkpoint monitors the kinetochore as a means to determine whether chromosomes have achieved metaphase alignment. As the kinetochore is the chromosomal site for microtubule attachment and contains molecular motors that specify various aspects of chromosome movement (6, 7), the checkpoint is likely to recognize biochemical signals at the kinetochore that differ between unaligned and aligned chromosomes (4). Consistent with this possibility, laser ablation of a single unattached kinetochore of a monopolar chromosome will abrogate the checkpoint arrest and the chromosomes aligned at the equator will separate as the cell enters anaphase (8). These experiments also demonstrate that checkpoint delay is mediated by an inhibitory signal from the unattached kinetochore. Interestingly, there is a reproducible lag of approximately 20 minutes from the time that the last chromosome becomes aligned till the onset of anaphase (8). This lag may define the time required to complete the biochemical reactions that are necessary for turning off the checkpoint induced block and the activation of the cyclosome/APC complex that specifies anaphase onset through ubiquitin-mediated proteolysis (9). To date, the nature of the signal that the kinetochore emits when it is not properly aligned has not yet been elucidated.

Kinetochores generate motive force through interactions with microtubules. For a bipolar attached chromosome, the tendency for each of the two oppositely-faced kinetochores to move towards their respective poles generates tension between the kinetochore pair. This contrasts with an unattached or a monopolar chromosome whereby little or no tension is generated at the kinetochores.

Elegant micromanipulation experiments performed on the trivalent sex chromosomes in the mantis spermatocyte (10) suggested that kinetochore tension serves as the signal which is detected by the mitotic checkpoint apparatus. During meiosis I, the two X chromosomes pair with a single Y chromosome. On occasion, one of the X's fails to pair and its mono-orientation delays anaphase. If kinetochore tension was supplied by using a microneedle to pull the unattached kinetochore in the direction of the opposite pole, the block to anaphase was lifted and all the chromosomes that were at the spindle equator separated and moved poleward. Again, there was a reproducible time-lag of approximately 15 minutes between application of kinetochore tension on the unaligned X chromosome and separation of the chromosomes aligned at the equator.

At a biochemical level, the inhibitory signal emitted from the unattached kinetochore is likely due to the specific phosphorylation of kinetochore proteins whose identities remain unknown. This hypothesis arises from the observation that a monoclonal antibody 3F3/2 (11), specific for undefined phosphoproteins, recognized differentially expressed phosphoepitopes at kinetochores in PtK cells (12). 3F3/2 was isolated from antibodies generated against mitotic frog extracts that had been incubated with ATP-γS so that proteins would be selectively thio-phosphorylated by mitotic kinases (11). Although the precise identity of the 3F3/2 epitope is unknown, it recognizes a small subset of undefined proteins that are phosphorylated in mitosis. It is unknown whether proteins that contain the 3F3/2 epitope overlap with the more familiar MPM-2 phosphoepitope that also appears primarily in mitosis (13). The connection between 3F3/2 phosphorylation and the mitotic checkpoint was based on the early observation that 3F3/2 staining was invariably more prominent at the kinetochore of unaligned chromosomes in PtK cells. In contrast, staining was lost or greatly diminished at the kinetochores of chromosomes that were aligned at the spindle equator. If mAb 3F3/2 was microinjected into PtK cells, the kinetochore-bound antibodies did not interfere with chromosome alignment but they failed to separate even though they were aligned at the spindle equator (14). Thus, the 3F3/2 phosphoepitope(s) at the kinetochore are probably not involved with kinetochore motility. Consistent with the idea that unaligned kinetochores emit a signal that blocks the onset of anaphase, the persistence of the 3F3/2 phosphorylated proteins at the kinetochore of aligned chromosomes, as a result of their association with the injected 3F3/2 antibody, was believed to maintain the checkpoint delay.

An important advance towards resolving the biochemical mechanism by which the checkpoint detects kinetochore tension was made by showing that tension regulated 3F3/2 phosphorylation (18). In a series of micromanipulation experiments using grasshopper spermatocytes, it was shown that when a chromosome was experimentally displaced from the metaphase plate, the intensity of 3F3/2 staining was increased over the levels found at aligned kinetochores. The same observation was made in unmanipulated cells, where the absence of tension resulting from the erroneous attachment of both kinetochores to the same pole produced intense 3F3/2 staining at kinetochores. Importantly, when tension was experimentally introduced by pulling one of the kinetochores of the maloriented chromosome, 3F3/2 staining was lost at the kinetochore under tension while bright staining was still detected at the sister kinetochore that was not under tension. The combined data strongly suggest that the phosphorylation states of kinetochore proteins are regulated by the amount of tension that is exerted at kinetochores. The issue of how 3F3/2 phosphoproteins (and other b)biochemical changes) at the kinetochore are detected is unknown.

As discussed above, during cell division, quality control mechanisms monitor critical events, such as DNA replication, cell growth, and chromosome segregation. In most cases, these checkpoint systems will override the underlying cell-cycle machinery and block advancement into the next stage of the cell cycle until certain requirements are met in the current cell cycle stage. Although key regulators of mitotic progression such as cyclinB/cdc2kinase and the cyclosome/Anaphase Promoting Complex (APC) have been identified and characterized, their relationships with mitotic checkpoint control remains unclear.

The present inventors have appreciated a need for the elucidation of the essential components involved in the regulation of cellular proliferation will provide novel targets for arresting mitosis in transformed cells. Such targets may be used to advantage to identify novel anti-proliferative agents.

SUMMARY OF THE INVENTION

This invention provides novel, biological molecules useful for identification, detection, and/or molecular characterization of components involved in the regulation of mitosis. According to one aspect of the invention, an isolated nucleic acid molecule is provided which includes an isolated open reading frame encoding a kinase of a size between about 115 and 130 kilodaltons. The encoded protein, referred to herein as huBUB1A, comprises a tripartite domain structure including an amino terminal kinetochore targeting domain, a central α-helical coil domain and a carboxy terminal kinase domain. The protein demonstrates significant binding affinity for CENP-E, a kinesin-related motor protein which localizes to the kinetochore where it functions to promote alignment of chromosomes at the spindle equator. HuBUB1A is a cytoplasmic protein during interphase but is assembled onto kinetochores prior to CENP-E sometime in prophase.

In a preferred embodiment of the invention, an isolated nucleic acid molecule is provided that includes a cDNA encoding a human BUB1A protein. In a particularly preferred embodiment, the human BUB1A protein has an amino acid sequence the same as Sequence I.D. No. 2. An exemplary huBUB1A nucleic acid molecule of the invention comprises Sequence I.D. No. 1.

According to another aspect of the invention, a second isolated nucleic acid molecule is provided which includes an isolated nucleic acid encoding a kinase of a size between about 110 and 140 kilodaltons and appears to be the human homolog of mouse BUB1. The encoded protein, referred to herein as huBUB1B, demonstrates significant binding affinity for CENP-F, a protein involved in the assembly and formation of a mature trilaminar kinetochore. HuBUB1B protein is detectable in nuclei of cells that are in the G2 stage of interphase. The HuBUB1B protein is subsequently localized it kinetochores sometime in prophase, prior in time to huBUB1A assembly at the kinetochore.

In a preferred embodiment of the invention, an isolated nucleic acid molecule is provided that includes a cDNA encoding a human BUB1B protein. In a particularly preferred embodiment, the human BUB1B protein has an amino acid sequence the same as Sequence I.D. No. 4. An exemplary huBUB1B nucleic acid molecule of the invention comprises Sequence I.D. No. 3.

According to yet another aspect of the invention, an isolated nucleic acid molecule is provided which includes an isolated open reading frame encoding a protein of a size between about 35 and 40 kilodaltons. The encoded protein, referred to herein as huBUB3, comprises five WD-40 motif repeats and complexes with huBUB1A and huBUB1B. The huBUB3 protein is a nuclear protein during interphase but also localizes to the kinetochores during mitosis.

In a preferred embodiment of the invention, an isolated nucleic acid molecule is provided that includes a nucleic acid sequence encoding a human BUB3 protein. In a particularly preferred embodiment, the human BUB3 protein has an amino acid sequence the same as Sequence I.D. No. 6. An exemplary huBUB3 nucleic acid molecule of the invention comprises Sequence I.D. No. 5.

According to another aspect of the present invention, an isolated nucleic acid molecule is provided, which has a sequence selected from the group consisting of: (1) Sequence I.D. No. 1; (2) a sequence specifically hybridizing with preselected portions or all of the complementary strand of Sequence I.D. No. 1; (3) a sequence encoding preselected portions of Sequence I.D. No. 1, (4) a sequence encoding part or all of a polypeptide having amino acid Sequence I.D. No. 2; (5) Sequence I.D. No. 3; (6) a sequence specifically hybridizing with preselected portions or all of the complementary strand of Sequence I.D. No. 3; (7) a sequence encoding preselected portions of Sequence I.D. No. 3, (8) a sequence encoding part or all of a polypeptide having amino acid Sequence I.D. No. 4; (9) Sequence I.D. No. 5; (10) a sequence specifically hybridizing with preselected portions or all of the complementary strand of Sequence I.D. No. 5; (11) a sequence encoding preselected portions of Sequence I.D. No. 5, (12) a sequence encoding part or all of a polypeptide having amino acid Sequence I.D. No. 6. Such partial sequences are useful as probes to identify and isolate homologues of the BUB genes of the invention. Accordingly, isolated nucleic acid sequences encoding natural allelic variants of the nucleic acids of Sequence I.D. Nos., 1, 3 and 5 are also contemplated to be within the scope of the present invention. The term natural allelic variants will be defined hereinbelow.

According to another aspect of the present invention, isolated human BUB1A, BUB1B and BUB3 proteins are provided. HuBUB1A is a protein kinase with a deduced molecular weight of between about 115 kDa and 130 kDa. HUBUB1A comprises a tripartite domain structure including an amino terminal kinetochore targeting domain, a central α-helical coil domain and a carboxy terminal kinase domain. The protein demonstrates significant binding affinity for CENP-E, a kinesin-related protein which localizes to the kinetochore. Human BUB1B protein is between about 110 and 140 kilodaltons and appears to be the human homolog of mouse BUB1. The encoded protein is a protein kinase and demonstrates significant binding affinity for CENP-F, a protein involved in the assembly and formation of a mature trilaminar kinetochore. HuBUB3 protein is between about 35 and 40 kilodaltons in size. HuBUB3 comprises five WD-40 motif repeats and complexes with huBUB1A. The huBUB3 protein also localizes to the kinetochores during mitosis.

In preferred embodiments of the invention, the proteins are of human origin, and have the amino acid sequences the same as Sequence I.D. Nos. 2, 4 and 6 respectively. In a further embodiment the proteins may be encoded by natural allelic variants of Sequence I.D. Nos. 1, 3, or 5.Inasmuch as certain amino acid variations may be present in human BUB proteins encoded by a natural allelic variants, such proteins are also contemplated to be within the scope of the invention.

According to another aspect of the present invention, antibodies immunologically specific for each of the three different human BUB proteins described hereinabove are provided.

In yet another embodiment of the invention, methods are provided for identifying novel therapeutic reagents for the regulation of mitosis. The method entails the use of nucleic acid fragments for expressing predetermined domains of the BUB proteins of the invention. Exemplary domains include the kinase domains of huBUB1A, and huBUB1B or the kinetochore binding domains of any of the three BUB proteins. Exemplary domains for huBUB1A, for example, include but are not limited to 1) the domain involved in huBUB3 binding between amino acids 194–466; 2) the domain that binds CENP-E between amino acids 408–546; 3) the domain by which huBUB1A binds the kinetochore between amino acids 1–466; and 4) the kinase domain of the protein between amino acids 644- to the carboxy terminus. The peptide domains are expressed, purified, and then immobilized on a solid support. The immobilized peptides are then exposed to test compounds. Compounds which bind the immobilized peptides will be further characterized in in vitro kinase assays and immunoprecipitation assays. Those compounds which demonstrate inhibition of kinase activity or disruption of BUB/kinetochore assembly, will then be assessed for inhibition of cell growth in tumor cells.

In an alternative embodiment, the test compounds may be immobilized to the solid support, and then exposed to the BUB proteins of the invention.

In yet another embodiment, full length BUB proteins may be utilized in the methods described above.

The methods of the invention also comprise the use of recombinant cell lines expressing one or a subset of the BUB genes of the invention. As above, test compounds will be added to the recombinant cells or lysates prepared therefrom, and disruption of BUB/kinetochore complex binding and/or inhibition of kinase activity will be assessed.

Various terms relating to the biological molecules of the present invention are used hereinabove and also throughout the specification and claims. The terms "specifically hybridizing," "percent similarity" and "percent identity (identical)" are defined in detail in the description set forth below.

With reference to nucleic acids of the invention, the term "isolated nucleic acid" is sometimes used.

This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the genomic DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., huBUB1A, huBUB1B or huBUB3), but which do not substantially recognize and bind other molecules in a sample containing a mixed population of antigenic biological molecules.

With respect to nucleic acids and oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). When used in reference to a double stranded nucleic acid, this term is intended to signify that the double stranded nucleic acid has been subjected to denaturing conditions, as is well known to those of skill in the art. In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The nucleic acids, proteins and antibodies of the present invention may be used to advantage as targets for the development of novel agents that inhibit aberrant cellular proliferation in tumor cells.

The human BUB molecules described above may also be used as research tools and will facilitate the elucidation of the mechanistic action of the novel genetic and protein interactions involved in the regulation of cell division and mitotic checkpoint control.

BRIEF DESCRIPTION OF THE DRAWINGS

FIGS. 1A and 1B represent the identification of the kinetochore binding domain in CENP-E. FIG. 1A is a schematic depiction of the CENP-E subfragments that were tested for kinetochore binding activity. FIG. 1B is a Western blot of lysates from Hela cells transiently transfected with constructs that express the subfragments shown in 1A.

FIG. 2A depicts yeast two-hybrid data showing the regions of CENP-E and huBUB1A that mediate the interaction. FIG. 2B shows the various regions of huBUB1A and CENP-E that were co-transfected into Hela cells to test for interaction in human cells. The various regions of huBUB1 that were epitoe-tagged were transfected into Hela cells and the transfacted huBUB1A proteins were immunoprecipitated from cell lysates with antibodies that only recognize the epitope-tag. Immunoprecipitates were then probed for the presence of endogenous CENP-E by western blots.

FIGS. 4A, 4B and 4C are immunoblots comparing the cell cycle expression profile of huBUB1A kinase in Hela cells. FIG. 4A illustrates that huBUB1A is post-translationally modified in mitotic shake-off and mitotically arrested cells, when compared to interphase. FIG. 4B depicts nocadozole block and release experiments which reveal that huBUB1A post-translational modification is lost upon exit from mitosis. FIG. 4C depicts the cell cycle expression profile of huBUB1A which reveals moderate increase in steady-state levels during G2 and M. The expression profiles of kinetochore proteins, CENP-E, CENP-F and hzw10 are also shown.

FIG. 5A compares the modification of huBUB1A between untreated interphase and mitotic cells versus nocodozole treated interphase and mitotically arrested cells. FIG. 5B depicts that phosphatase treatment of the mitotic form of huBUB1A alters its migration to that seen for interphase huBUB1A.

FIG. 7A shows the distribution of huBUB1A and CENP-E from interphase through metaphase. FIG. 7B shows the distribution of huBUB1A and CENP-E from metaphase to telophase.

FIG. 8A is a Western blot of Hela lysates obtained from untreated and nocadozole treated interphase end mitotic Hela cells. FIG. 8B is a set of micrographs which show that mitotic Hela cells expressing gfp or protein A: huBUB3 fusions are targeted to kinetochores. Gfp was visualized by autofluorescence. Protein A: huBUB3 was detected by staining cells with Texas Red conjugated human IgG. DNA was stained with DAPI and visualized by UV illumination.

FIG. 9 shows Western blotting experiments illustrating that huBUB1A and huBUB1B are associated with huBUB3. HuBUB1A and huBUB1B immunoprecipitates from mitotic Hela cells were probed with huBUB1A and huBUB1B (lanes 1 and 2, top panels, respectively) and huBUB3 (lanes 1 and 2, bottom panels) antibodies.

FIGS. 10A and 10B are a series of autoradiographs and western blots which reveal that while HuBU31A exhibits no detectable autokinase activity in cells which have been synchronized at different stages of the cell cycle, the protein is expressed at similar levels throughout the cell cycle. However, as cells entered mitosis, demonstrable huBUB1A autokinase activity was observed (FIG. 10A). FIG. 10B shows autoradiograms and western blots which present the results of similar kinase assays on huBUB1B kinase. The data show that huBUB1B exhibited autokinase activity throughout the cell cycle and the level of kinase activity approximated the steady state levels of the protein as determined by western blot.

FIG. 13 is the amino acid sequence of human BUB1A kinase (Sequence I.D. No. 2).

FIG. 14 is the amino acid sequence of human BUB1B kinase (Sequence I.D. No. 4).

FIG. 15 is the amino acid sequence of human BUB3 (Sequence I.D. No. 6).

DETAILED DESCRIPTION OF THE INVENTION

Figure 2A:
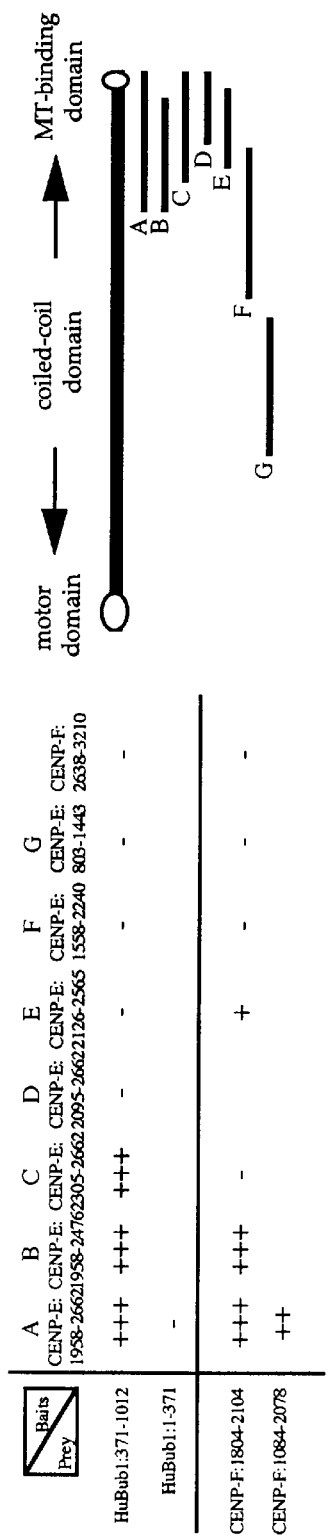
FIGS. 2A and 2B show the the strategy utilized to map the domains in huBUB1A and CENP-E that specifically interact.

Mammalian homologs of yeast spindle checkpoint genes and their encoded proteins are disclosed herein. The characterization of the structural components that specify kinetochore motility in animal cells provides new mechanistic insights into how chromosomes achieve alignment at the spindle equator. To date, the molecular connection between the mechanical function at kinetochores and the mitotic checkpoint proteins remains unclear. The data presented herein illustrate that such a connection has been established. A human BUB1A kinase that associates with the CENP-E kinetochore motor has been identified. HuBUB1A is hyperphosphorylated in cells blocked in mitosis. A second kinase, huBUB1B, has also been isolated. This kinase is also involved in mitotic checkpoint control and associates with the kinetochore binding domain of CENP-F. Additionally, the human BUB3 homolog has been cloned. The data show that it is a subunit of huBUB1A and both proteins are located at kinetochores during mitosis.

The examination and identification of candidate proteins that are phosphorylated by the huBUB kinases will reveal the kinetochore phosphoproteins that are recognized by the checkpoint system as well as effectors of the signaling pathway that delay activation of the cyclosome/APC proteolysis machinery and thus block chromosome separation and anaphase onset. It appears that huBUB1A kinase functions as a sensor to determine whether chromosomes have aligned properly and then relays this information to the global regulatory machinery that specifies mitotic progression. The methods provided herein will facilitate the identification of therapeutic agents that cripple the mitotic checkpoint pathway and thus significantly enhance the sensitivity of tumor cells to existing anti-mitotic compounds.

I. Preparation of Human DUB-Encoding Nucleic Acid Molecules, BUB Proteins, and Antibodies Thereto A. Nucleic Acid Molecules Nucleic acid molecules encoding the human BUB proteins of the invention may be prepared by two general methods: (1) synthesis from appropriate nucleotide triphosphates, or (2) isolation from biological sources. Both methods utilize Protocols well known in the art. The availability of nucleotide sequence information, such as cDNAs having Sequence I.D. Nos. 1, 3, or 5 enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 3.9 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 3.9 kb double-stranded molecule. A synthetic DNA molecule so constructed may then be cloned and amplified in an appropriate vector.

Nucleic acid sequences encoding the human BUB proteins may be isolated from appropriate biological sources using methods known in the art. In a preferred embodiment, a cDNA clone is isolated from a cDNA expression library of human origin. In an alternative embodiment, utilizing the sequence. information provided by the cDNA sequence, human genomic clones encoding BUB proteins may ba isolated. Alternatively, cDNA or genomic clones having homology with BUB1A, BUB1B or BUB3 may be isolated from other species using oligonucleotide probes corresponding to predetermined sequences within the BUB encoding nucleic acids.

In accordance with the present invention, nucleic acids having the appropriate level of sequence homology with the protein coding region of sequence I.D. No. 1 may be identified by using hybridization and washing conditions of appropriate stringency. For example, hybridizations may be performed, according to the method of Sambrook et al., (supra) using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \log [Na+] + 0.41(\% G+C) - 0.63 (\% \text{formamide}) - 600/\#bp \text{ in duplex}$$

As an illustration of the above formula, using [Na+]= [0.3683] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in a plasmid cloning/ expression vector, such as pBluescript (Stratagene, La Jolla, Calif.), which is propagated in a suitable E. coli host cell.

BUB-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting or isolating BUB qenes. Antisense nucleic acid molecules may be targeted to translation initiation sites and/or splice sitars to inhibit the production of the BUB genes of the invention. Such antisense molecules are typically between 15 and 30 nucleotides and length and span the translational start site of BUB encoding mRNA molecules.

It will be appreciated by persons skilled in the art that variants (e.g., allelic variants) of these sequences exist in the human population, and must be taken into account when designing and/or utilizing oligos of the invention. Accordingly, it is within the scope of the present invention to encompass such variants, with respect to the BUB sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a human population. The usage of different wobble codons and genetic polymorphisms which give rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

B. Proteins

Full-length huBUB1A, huBUB1B or huBUB3 proteins of the present invention may be prepared in a variety of ways, according to known methods. The proteins may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding BUB proteins enables production of the proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or Gibco-BRL, Gaithersburg, Md.

Alternatively, according to a preferred embodiment, larger quantities of BUB proteins may be produced by expression in a suitable prokaryotic or eukaryotic system. For example, part or all of a DNA molecule, such as a cDNA having Sequence I.D. No. 1, 3 or 5 may be inserted into a plasmid vector adapted for expression n a bacterial cell, such as *E. colli*. Such vectors comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

The human BUB proteins produced by gene expression in a recombinant procaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6–8 histidine residues at their N-terminus or C-terminus. Alternative tags may comprise the FLAG epitope or the hemagglutinin epitope. Such methods are commonly used by skilled practitioners.

Polypeptide variants may also be prodaced in accordance with the present invention. Two protein sequences are said to be identical when they shared the same amino acid sequences. Derivative or mutants of the amino acid sequences shown in SEQ ID No: 2, 4 or 6 may comprise amino acid sequences which share greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in Sequence I.D. Nos.2, 4, or 6 by insertion, addition, substitution or deletion of 1 amino acid, 2, 3, 4, 5–10, 10–20, 20–30, 30–40, 40–50, 50–100, 100–150, or more than 150 amino acids.

A polypeptide according to the present invention may be used in screening for molecules which affect or modulate its activity or function. Such molecules may be useful in a therapeutic (possibly including prophylactic) context.

The present invention also provides antibodies capable of immunospecifically binding to proteins of the invention. Polyclonal antibodies directed toward human BUB proteins may be prepared according to standard methods. In a preferred embodiment, monoclonal antibodies are prepared, which react immuiiospecifically with the various epitopes of the BUB proteins described herein. Monoclonal antibodies may be prepared according to general methods of Köhler and Milstein, following standard protocols. Polyclonal or monoclonal antibodies that immunospecifically interact with BUB proteins can be utilized for identifying and purifying such proteins. For example, antibodies may be utilized for affinity separation of proteins with which they immunospecifically interact. Antibodies may also be used to immunoorecipitate proteins from a sample containing a mixture of proteins and other biological molecules.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragments consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention. Other uses of anti-BUB antibodies are described below.

II. Uses of BDB-Encoding Nucleic Acids, BUB Proteins and Antibodies Thereto

Cellular signalling molecules have received a great deal of attention as potential prognostic indicators of neoplastic disease and as therapeutic agents to be used for a variety of purposes in cancer chemotherapy. The BUB proteins of the invention are intimately involved in the regulation of mitosis. The biochemical and molecular interactions of the BUB genes and proteins involved in mitotic checkpoint control provide novel targets for the development of reagents that hypersensitize tumor cells to conventional anti-mitotic compounds.

Additionally, BUB nucleic acids, proteins and antibodies thereto, according to this invention, may be used as research tools to identify other proteins that are intimately involved in the mitotic checkpoint. Biochemical elucidation of molecular mechanisms at the kinetochore which control mitosis will facilitate the development of novel anti-mitotic agents that may be used to inhibit the aberrant cellular proliferation of tumor cells.

A. BUB-Encoding Nucleic Acids

BUB-encoding nucleic acids may be used for a variety of purposes in accordance with the present invention. BUB-encoding DNA, RNA, or fragments thereof may be used as probes to detect the presence of and/or expression of genes encoding BUB proteins. Methods in which BUB-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The BUB-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, BUB-encoding nucleic acids may be used to advantage to identify and characterize other genes of varying degrees of relation to the BUB genes of the invention thereby enabling further characterization of the mitotic checkpoint control system. Additionally, they may be used to identify genes encoding proteins that interact with BUB proteins (e.g., by the "interaction trap" technique), which should further accelerate identification of the components involved in mitotic checkpoint control.

Nucleic acid molecules, or fragments thereof, encoding BUB genes may also be utilized to control the production of BUB proteins, thereby regulating the amount of protein available to participate in mitotic checkpoint control reactions. As mentioned above, antisense oligonucleotides corresponding to essential processing sites in BUB-encoding mRNA molecules may be utilized to inhibit BUB protein production in targeted cells. Alterations in the physiological amount of BUB proteins may dramatically affect the activity of other protein factors involved in the regulation of mitosis.

The availability of BUB encoding nucleic acids enables the production of strains of laboratory mice carrying part or all of the BUB genes or mutated sequences thereof. Such mice may provide an in vivo model for cancer. Alternatively, the BUB nucleic acid sequence information provided herein enables the production of knockout mice in which the endogenous genes encoding BUB1A, BUB1B or BUB3 have been specifically inactivated. Methods of introducing transgenes into laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role BUB proteins play in mitosis during embryonic development.

Exemplary approaches for detecting Bub encoding nucleic acids or polypeptides/proteins include:

a) comparing the sequence of nucleic acid in the sample with the BUB nucleic acid sequence to determine whether the sample from the patient contains mutations; or b) determining the presence, in a sample from a patient, of the polypeptide encoded by a BUB gene.of the invention and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal BUB gene or from known mutations thereof; or, d) using a specific binding member capable of binding to a BUB nucleic acid sequence (either normal sequence or known mutated sequence), the specific binding member comprising nucleic acid hybridizable with a BUB Esequence, or substances comprising an antibody domain with specificity for a native or mutated BUB nucleic acid sequence or the polypeptide encoded by it, the specific binding member being labelled so that binding of the specific binding member to its binding partner is detectable; or, e) using PCR involving one or more primers based on normal or mutated BUB gene sequences to screen for normal or mutant BUB genes in a sample from a patient.

As described above, BUB-encoding nucleic acids are also used to advantage to produce large quantities of substantially pure BUB proteins, or selected portions thereof.

B. BUB Proteins and Antibodies

Purified BUB proteins, or fragments thereof, may be used to produce polyclonal or monoclonal antibodies which also may serve as sensitive detection reagents for the presence and accumulation of BUB proteins (or complexes containing BUB proteins) in mammalian cells. Recombinant techniques enable expression of fusion proteins containing part or all of BUB proteins. The full length proteins or fragments of the proteins may be used to advantage to generate an array of monoclonal antibodies specific for various epitopes of BUB proteins, thereby providing even greater sensitivity for detection of BUB proteins in cells.

Polyclonal or monoclonal antibodies immunologically specific for BUB proteins may be used in a variety of assays designed to detect and quantitate the proteins. Such assays include, but are not limited to: (1) flow cytometric analysis; (2) immunochemical localization of BUB proteins in tumor cells; and (3) immunoblot analysis (e.g., dot blot, Western blot) of extracts from various cells. Additionally, as described above, anti-BUB antibodies can be used for purification of BUB proteins and any associated subunits (e.g., affinity column purification, immunoprecipitation).

Methods for Identifying Novel Therapeutic Agents for Inhibiting Mitotic Events in Tumor Cells According to another aspect of the invention, methods of screening candidate compounds to identify drugs which regulate mitosis are provided. Anti-mitotic drugs are often used in the treatment of cancer. These drugs are primarily microtubule poisons which block cells in mitosis by inhibiting spindle (made up of microtubules) formation and thus disrupt chromosome alignment. These cells arrest in mitosis when spindle assembly is disrupted because the cells initiate a failsafe program called the checkpoint. The checkpoint is a natural mechanism that delays cells from progressing through mitosis when spindle assembly or chromosome alignment is incomplete. This delay provides the cell time to correct these defects before proceeding though the cell cycle.

Anti-mitotic drugs arrest cells in mitosis because an active checkpoint mechanism senses the absence of spindles and unaligned chromosomes and thus halts mitotic progression. This checkpoint is temporary and in cases where the defects are not corrected, the cells eventually undergo apoptosis.

The BUB polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a BUB polypeptide or fragment and the agent being tested, or examine the degree to which the formation of a complex between a BUB polypeptide or fragment and a known ligand is interfered with by the agent being tested.

Another technique for drug screening provides high throughput screening for compounds having suitable binding affinity to the BUB polypeptides of the invention and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with BUB polypeptides and washed. Bound BUB polypeptide is then detected by methods well known in the art.

Purified BUB proteins or fragments thereof may be coated directly onto plates for use in the aforementioned drug screening techniques. However, non-neutralizing antibodies to the polypeptide can be used as capture antibodies to immobilize the BUB polypeptide on the solid phase.

This invention also contemplates the use of competitive drug screening assays in which neutralizing antibodies capable of specifically binding the BUB polypeptide compete with a test compound for binding to the BUB polypeptide or fragments thereof. In this manner, the antibodies can be used to detect the presence of any peptide which shares one or more antigenic determinants of the BUB polypeptide.

A further technique for drug screening involves the use of host eukaryotic cell lines or cells (such as described above) which have a nonfunctional BUB. gene(s). These host cell lines or cells are defective at the BUB polypeptide level. The host cell lines or cells are grown in the presence of drug compound. The rate of growth of the host cells is measured to determine if the compound is capable of regulating the growth of BUB defectivecells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19–21. In one approach, the three-dimensional structure of a protein of interest (e.g., BUB polypeptide(s)) or, for example, of the BUB-DNA complex, is determined by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527–533). In addition, peptides (e.g., BUB polypeptide) may be analyzed by an alanine scan (Wells, 1991) Meth. Enzym. 202:390–411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved BJB polypeptide activity or stability or which act as inhibitors, agonists, antagonists, etc. of BUB polypeptide activity. By virtue of the availability of cloned BUB sequences, sufficient amounts of the BUB polypeptide(s) may be made available to perform such analytical studies as x-ray crystallography. In addition, the knowledge of the BUB protein sequences provided herein will guide those employing computer modeling techniques in place of, or in addition to x-ray crystallography.

From the foregoing discussion, it can be seen that BUB-ancoding nucleic acids, BUB expressing vectors, BUB proteins and anti-BUB antibodies of the invention cain be used to detect BUB gene expression and alter BUB protein accumulation for purposes of assessing the genetic and protein interactions involved in the mitotic checkpoint control pathway. This information, in turn, provides the foundation for identifying novel therapeutic agents which may be used to advantage in the treatment of cancer or other disorders characterized by aberrant cell growth.

The examples presented below are provided to illustrate certain embodiments of the invention. They are not intended to limit the invention in any way. The following protocols were utilized in practicing the methods of the present invention.

Cloning and Analysis of cDNA

The full-length huBUB1A cDNA was isolated by extending the yeast two-hybrid Int-57 clone towards the 5' end by RACE (Amplifinder, Clontech) using. TJY 300 (5' GCT-GATCACCTGTTCTTTCTTGCTC 3'; SEQ ID NO: 7) as the 3' primer and nested 5' primers AP1 and AP2 that are provided in the kit. The PCR reactions were performed using conditions specified by the manufacturer. The 5' RACE products were digested with proteinase K for 2 to 4 hours at 37° C., precipitated, gel-purified and cloned into pGEM-T (Promega, Wisconsin). DNA sequence was determined in both directions with an automated sequencer (Applied Biosystems, Foster City, Calif.). The interactor cDNA was also extended by using the 5' portion of Int-57 (800 bp EcoRI HindIII fragment) to screen a λgt11 human breast carcinoma cDNA library (Clontech) by hybridization. DNA sequence of the phage clone matched and authenticated the RACE product. Northern blots of total and polyA RNA from human K562 cells were hybridized to the same probe used for library screening. DNA probes were radiolabelled by random priming and hybridizations were performed in 5×SSPE/5×Denhardt's/0.5% SDS/0.1 mg/ml sheared sonicated salmon spern DNA at 65° C. Filters were washed twice with 1×SSC/0.1% SDS at room temperature for 30 minutes, 0.2×SSX/0.1% SDS between 60° C. to 65° C. for 10 minutes and the filter was exposed to X-ray film. DNA and protein sequences were analyzed with MacVector 6.0 (Oxford Molecular Biology, Oxford, UK), BLAST and BEAUTY.

Full-length huBUB3 cDNA was isolated by RT-PCR (Amplifinder, Clontech, Palo Alto, Calif.) using oligos designed from available EST cDNA sequence information. To obtain full length huBUB3 by 5' RACE, the 3' oligo tjy 309 (5' ATCGTCGACTCCACCATTGGGGAGTACG 3'; SEQ ID NO: 8) was used in conjunction with the nested 5' Clontech Ap1 and Ap2 primers.

huBUB1B was first identified as Fint 309 in a yeast two-hybrid screen, utilizing the 572 amino acid kinetochore-bitiding region of CENP-F (amino acids 2638–3210) as the bait. The fragment of huBUB1B which was identified from the yeast two-hybrid library plasmid starts at nucleotide* 1990 (amino acid 663) of the huBUB1B sequence and the fragment was approximately 1500 nucleotides long. The sequence of huBUB1B from the two-hybrid clone was verified by comparison to two sequences in the EST database, R94348 and EST 187416 (which correspond roughly to nucleotides 900–3500, and 2250–3150, respectively). To obtain full-length huBUB1B cDNA, primers were designed for 3' and 5' race:

3' race: 5' CGG GAT CCA GGT CCA AAA GCC TGC CAA CC 3' (nucleotides 2566–2586, with BamHI site for cloning; SEQ ID NO: 9)

5' race: single and nested single: 5' CGG GAT CCT GCT GGG AGC CTA CAC TTG 3' (nucleotides 1075–1055, with BamHI site for cloning; SEQ ID NO: 10)

nested: 5' CGG GAT CCA AGC CTC AAC GCC AAC CTC TG 3' (nucleotides 2167–2147, with BamHI site for cloning; SEQ ID NO: 11)

Race was done with a Clonetech Marathon cDNA Amplification kit, following kit instructions. The cDNA amplified was a K562 cell cDNA library, for the single race reactions, this was amplified for 30 cycles (94° C. for 30 sec, 60° C. for 4 min) with the specific 5' or 3' race primer and the AP1 primer from the kit. The resulting reaction was diluted 1:50 and used for amplification with the specific 5' or 3' race primer and the AP2 primer from the kit, following the PCR protocol above. For the nested race, the K562 cDNA was amplified first with the most internal primer (the nested primer above) and the AP1 primer from the kit. The product from this reaction was then amplified with the single 5' specific primer above and the AP2 primer from the kit. All PCR protocols were as above. Race products were isolated and subcloned into the pGEM-T Easy Vector (Promega) and DNA was isolated for automated sequencing at the FCCC DNA sequencing facility.

Antibodies and Immunodetection

For production of huBUB1A antibodies, the C-terminal 642 amino acids of huBUB1A were fused to myelin basic protein (MBP) in the PMAL expression vector (New England Biolabs, Beverly, MA) and the purified fusion protein was used to immunize rats and rabbits. The corresponding segment of huBUB1 was fused to glutathione-S-transferase (GST) (Pharmacia, N.J.) and the purified fusion protein GST: huBUB1 was covalently attached to Affi-gel 10 as per manufacturer's instructions. Serum was incubated with the affinity column overnight at 4° C. After extensive washing to remove non-specifically bound antibodies, the huBUB1 antibodies were eluted with several column volumes of 0.2M glycine pH 2.5. The eluate was immediately neutralized with 0.5M Tris pH 8.5. The peax protein fractions were pooled, concentrated and stored in 50% glycerol/PBS at −80° C.

Antibodies immunologically specific for huBUB1B were generated using two regions of the protein which were selected for their dissimilarity to huBUB1A. Region one encompasses amino acids 306–444 (nucleotides 918–1133), and region two encompasses amino acids 784–864 (nucleotides 2353–2594). Both gene fragments were cloned into the pMAL expression vector (New England Biolabs). Fusion protein was produced in BL21(DE3) bacteria by induction with 1 mM IPTG. After 3 hours at 37° C., cells were harvested, lysed, and both proteins were immunoprecipitated from the soluble fraction of the bacteria with amylose resin for 60 min at 4° C., washed extensively with PBS and boiled off the beads. SDS-PAGE slab gels were run of the purified proteins, and protein was cut out of the gel to use as injection material in rabbits and rats.

Tissue cultured cells (Hela) were lysed in buffer containing (50 mM Tris-Cl pH 7.5, 150 mM NaCl, 1% NP-40) with protease inhibitors (AEBSF, leupeptin, aprotinin, chymostatin) and in some cases phosphatase inhibitors (NaF, okadaic acid, vanadate, microcystin). Lysates were spun at 13,000×g for 10 minutes ar 4° C. and the clarified supernatant was used for western blots or immunoprecipitation. Immunoprecipitations were performed by incubating the lysates with 5 ug/ml of the primary antibody at 4° C. from 4 hours to overnight. Protein A or Protein G sepharose beads (Sigma, St. Louis, Mo.) were used to precipitate the antibody:antigen complex. Western blots were performed exactly as specified by the manufacturer (Tropix).

For western blots, cell lysates (30 to 100 ug total protein) or immunoprecipitates were resolved in by SDS PAGE, transferred to PVDF membrane and probed with antibodies diluted to 1–3 ug/ml final concentration. After washing to remove excess primary ; antibodies, filters were incubated with 1:30,000 dilution of alkaline phosphatase conjugated anti-rat or anti-rabbit antibodies conjugated to alkaline phosphatase (Jackson Immunoresearch) and processed for chemiluminescence detection according to manufacturer's instructions (Western Light Tropix).

For immunofluorescence staining, cells grown on glass coverslips were extracted in KB (50 mM Tris-HCl, pH 7.4, 150 mM NaCl, 0.1% BSA) with 0.2% Triton X-100 for 5 minutes at room temperature and washed in KB for 5 minutes, then fixed with 3.5% paraformaldehyde buffered in phosphate buffered saline (PBS) at pH 6.8. In some cases, the process was reversed so that samples were fixed and then extracted. Samples were incubated with primary antibody (1 to 3 ug/ml in KB) in a humidified 37° C. incubator for 30 to 60 minutes, washed in KB at room temperature for 5 to 10 minutes and incubated with appropriate secondary antibodies conjugated with fluorochrome such as FITC, Texas Red or Cy-5. Nuclei and chromosomes were counterstained with 4', 6' diamino phenylindole (DAPI, Sigma). Coverslips were mounted 0.1% para-phenylenediamine in glycerol and scanned for transfected cells using a Nikon Microphot SA equipped with epifluorescence optics. Cells were visualized with a 100× Plan Neofluor objective and images were captured with a TEC-1 CCD camera (DAGE-MTI, Michigan City, Id.) that was controlled with a Macintosh Quadra 650 running IPLab Spectrum (Signal Analytics). Image processing was performed using Adobe Photoshop 4.0.

Kinase Assay

HuBUB1A and huBUB1B immunoprecipitates were washed 5 times in lysis buffer (see above for immunoprecipitations) and then 3 times in kinase buffer (25 mM Tris-Cl pH 7.8, 5 mM Mg and $MnCl_2$, 50 mM ATP, phosphatase inhibitors). Substrate proteins or peptides are added along with 50 uCi $\gamma^{32}$P-ATP (SPA>6000 mCi/umole) and the reaction is incubated at 37° C. for 30 minutes and then stopped by addition of SDS gel sample buffer. The kinase reaction is resolved by SDS PAGE and processed for autoradiography. Kinase assays may also be performed using purified, recombinantly expressed proteins.

Transient Transfection

Monolayer cells were grown in DMEM with 10% fetal calf serum (FCS) at 37° C. in 5% $CO_2$. Hela cells were transiently transfected by calcium phosphate precipitation (Chen and Okayama, 1987). Thirty-six hours after transfection, cells are harvested in NP40 lysis buffer [50 mM Tris pH 8, 150 mM NaCl, 1%NP40, 1 mM PMSF, and 1 mg/ml protease inhibitors (leupeptin, aprotinin and pepstatin)]. ProA-CENP-E fusion proteins were immunoprecipitated with 25 ul of a 50% slurry of human IgG sapharose (Pharmacia).

Cells were also transfected by lipofection (LT2, PanVera). Hela cells were washed briefly with serum-free OptiMEM (Gibco-BRL, Gaithesberg, Md.) and incubated with the DNA-lipid complexes in OptiMEM for 6 hours. The lipid-DNA complexes were washed away and replaced with complete medium (DMEM, 10% fetal calf serum). After 12 to 36 hours, transfected cells were processed for western blots or immunofluorescence staining.

Yeast Two-hybrid Screening

The two-hybrid screen was performed precisely as described by Golemis, et.al., 1996. The yeast strains EGY191 and EGY48 as well as yeast expression vectors pEG202, pJG4-5, and pSH18-34 were kindly provided by E. Golemis. The gal-inducible HeLa cDNA expression library that was cloned in pJG4-5 was a kind gift from R. Brent (Zervos, et. al. 1993). The CENP-E bait containing aiminio acids 1958 to 2662 was isolated as a BamHI/SalI fragment from pWS4proA:CENP-E$^{1958-2662}$ and inserted into the BamHI/XhoI sites of pEG202 to create a carboxy terminal fusion with amino acids 1–202 of the lexA DNA binding domain. The resultant pEG202-CENP-E$^{1958-2662}$ was transformed into EGY191 along with the lacZ reporter plasmid pSH18-34. Transformants which did not activate the single-copy leu2 and the multi-copy lacZ reporter genes were then transformed with the Hela cDNA library. Transformants were selected on Ura$^-$, His$^-$, and Trp$^-$ minimal glucose media to select for the plasmids pEG202-CENP-E$^{1958-2662}$, pSH18-34 and the pJG4-5 library. Ura$^+$, His$^+$, and Trp$^+$ transformants were harvested from the plates, aliquoted and stored at −80° C. Transformants (4×10$^7$) were replated onto Ura$^-$, His$^-$, Trp$^-$, and Leu$^-$ galactose/raffinose media to select for cDNAs that expressed CENP-E interactors that activated the leu2 gene. Approximately 500 primary Leu$^+$ colonies were picked and streaked onto X-gal minimal media that contained either glucose or galactose to test for activation of the pSH18-34lacZ reporter. Approximately 100 colonies that were blue on galactose media but white on glucose media were identified and the pJG4-5 interactor cDNAs along with its trp selectable marker were isolated by transforming trp$^-$ E. coli XC8 and selecting for trp prototrophy. In some cases, the cDNA was directly amplified from the yeast mini-prep DNA by PCR using primers that flank the cloning site; EGY175, 5' CTGAGTGGAGATGCCTCC 3' (SEQ ID NO: 12); RY220, 5' CTGGCAAGGTAGA-CAAGCCG 3' (SEQ ID NO: 13). Mini-prep plasmid DNA isolated from E. coli KC8, or PCR products were digested with several restriction enzymes and grouped according to their digestion patterns.

Specificity of the interactors was independently verified by retransforming the interactor cDNAs back into EGY191 along with pSH18-34 (lacZ reporter) and either pEG202-CENP-E$^{1958-2662}$, or other LexA:baits such as pRFM1 (Drosophila bicoid), pEG202-K-rev (gifts of E. Golemis), or pEG202 CENP-F10-2 (the carboxy terminus of CENP-F, provided by S. Jablonski). cDNAs that only interacted with pEG202-CENP-E$^{1958-2662}$ according to galactose-dependent Leu$^+$/lacZ$^+$ expression were sequenced by an automated sequencer (ABI) using primers EGY175 and RY220.

MaDping the Regions in CENP-E that Interact with huBUB1A and CENP-F

To delineate the region of CENP-E that specified interactions, with Int-484 (CENP-F) and Int-57 (huBUB1), segments of CENP-E that were used to map the kinetochore binding region were cloned into the plasmid pEG202. Fragments were digested from the appropriate pWSproA constructs (see above) with BamHI/SalI and ligated into BamHI/XhoI digested pEG202 to create in-frame fusions with lexA. All of the resultant baits, along with pSH18-34 (lacZ reporter) were transformed into EGY48 which contains 6 lexO sites in the promoter of the single copy leu2 reporter gene. The transformants were verified to not self-activate the reporter genes on galactose media and they were then transformed with pJGInt-57 (huBUB1) and pJG Int-484 (CENP-F). Four to five colonies from each transformation were restreaked onto minimal ura-, his, trp-, X-gal plates containing glu or gal/raf and also onto minimal ura-, his-, trp-, leu-, gal/raf or glu plates. Plates were incubated at 30° C. and inspected 4, 8, 12 and 24 hours later for blue color formation on the X-gal plates. Plates were inspected from 18 to 36 hours for growth on leu-media.

Mitotic Checkpoint Assay

Asynchronous tissue culture cells are incubated in the presence of microtubule inibitors such as nocodazole (60 ng/ml final concentration) and a mitotic indtex is determined after overnight incubation in the drug. Cells expressing mutant forms of huBUB1A or microinjected with huBUB1A antibodies are treated in the same way. Apoptotic cells are determined by visualizing condensed and fragmented nuclei by DAPI staining.

EXAMPLE I

Characterization of the Molecular Interactions Between CENP-E and the Kinetochore To identify proteins within the kinetochore that normally form a complex with CENP-E, the domain within CENP-E that specified kinetochore binding was characterized and then used as a tool to search for proteins with which it binds. Different regions of CENP-E were fused to the IgG binding domain of protein A (FIG. 1A) or gfp, (not shown) and the intracellular distribution of the fusion proteins examined in transfected mitotic cells. Western blotting of lysates prepared from transiently transfected Hela cells confirmed that all of the constructs expressed the correct size protein at equivalent levels (FIG. 1B, proA:fusions). Inspection of mitotic cells showed that segments derived from the C-terminal portion of CENP-E directed gfp and proA to the kinetochore. Kinetochore binding was not observed with fragments that spanned the remainder of the molecule including the amino terminus. These experiments demonstrated that the kinetochore binding domain of CENP-E is localized between amino acids 2126–2565 and is separable from the C-terminal microtubule binding domain. The kinetochore binding domain was not detectably phosphorylated during mitosis in vivo suggesting that phosphorylation of CENP-E is not required for interaction with other kinetochore proteins.

To identify proteins that associate with the kinetochore binding domain of CENP-E, the C-terminal 704 amino acids were used as bait to screen a Hela cDNA library using yeast two-hybrid technology. The CENP-E bait was fused to the DNA binding domain of lexA and stable accumulation of the fusion protein in yeast was confirmed by Western blotting. It should be noted that expression of the bait alone was insufficient to induce the expression of the leu2 and lacZ reporter genes that were used to detect protein interactions. Potential interactors were selected by plating the yeast transformants onto leu media that also contained galactose to induce expression of the cDNA library. Leu+ were restreaked onto leu-media containing galactose or glucose to confirm that the interaction was gal-dependent and thus was specified by expression of the cDNA. In addition, the leu+ transformants were also tested for their ability to activate a lacZ reporter in the presence of galactose to verify the results from the leu 2 reporter. Approximately 500 primary leu+ transformants were isolated. The number of positive transformants was reduced to 200 after retesting. Comparison of the HaeIII digestion pattern of the PCR products derived from these 200 clones showed that most of them were isolated multiple times (3 to 17). Amongst them were a known kinetochore protein, CENP-F and a kinase that exhibited the highest similarity to the yeast BUB1 kinase.

Segments of CENP-E and CENP-F assayed in the two hybrid screen are predicted to mediate extensive coil-coil interactions. The specificity of these interactions was further tested with coil-coil segments that were derived from other regions of these proteins. Thus, the CENP-F interactor failed to interact with a coil-coil segment that was derived from the central stalk region of CENP-E (FIG. 2A, segment E, F). Likewise, the CENP-E kinetochore binding domain failed to interact with other helical portions of CENP-F. The specificity of the interaction between CENP-F (amino acids 1834 to 2104) and the C-terminal 704 amino acids of CENP-E suggested that CENP-F is one of the proteins that binds to CENP-E at the kinetochore. This possibility is supported by the observation that CENP-F appears at kinetochores before CENP-E.

Figure 2B:
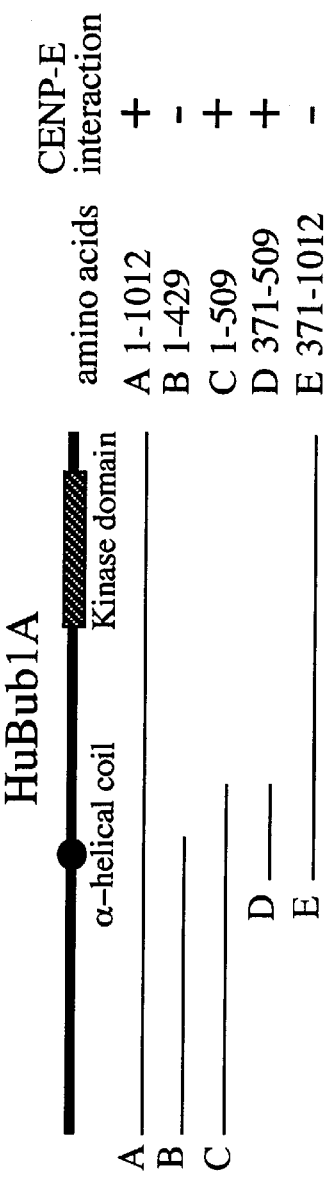

A similar analysis with the huBUB1A interactor clone showed that it exhibited specificity for the kinetochore binding domain of CENP-E. Interactions with other portions of CENP-E were not detected (FIG. 1A, fragments E, F, and G). Inasmuch as the amino terminal portion of huBUB1 did not exhibit detectable interaction with CENP-E, it appears that elements within the C-terminal half of huBUB1A specifically recognizes elements within the CENP-E kinetochore binding domain (FIG. 2A). To localize the region within huBUB1A that specifies its interactions with CENP-E, different regions of huBUB1A (FIG. 2B) were transfected into Hela cells and their co-immunoprecipitation with either endogenous CENP-E or a co-transfected kinetochore binding domain was assessed. The cumulative results show that segment D from the central region of huBUB1A which is predicted to form a coil-coil domain, specifies stable association with the kinetochore binding domain of CENP-E in Hela cells. The nucleic acid sequence of huBUB1A is set forth below as Sequence I.D. No. 1:

GTTAGGGAGT CGTGTGCGTG CCTTGGTCGC
TTCTGTAGCT CCGAGGGCAG GTTGCGGAA-
GAAAGCCAGG CGGTCTGTGG CCCAGAAGAA
AGGCCTGCAG CAGGACGAGG ACCTGAGCCA
GGAATGCAGG ATGGCGGCGG TGAAAAAGGA
AGGGGGTGCT CTGAGTGAAG CCATGTCCCTG-
GAGGGAGAT GAATGGGAAC TGAGTAAAGA
AAATGTACAA CCTTTAAGGC AAGGGCGGAT-
CATGTCCACG CTTCAGGGAG CACTGGCACA
AGAATCTGCC TGTAACAATA CTCTTCAGCAG-
CAGAAACGG GCATTTGAAT ATGAAATTCG
ATTTTACACT GGAAATGACC CTCTGGAT-
GTTTGGGATAGG TATATCAGCT GGACAGAGCA
GAACTATCCT CAAGGTGGGA AGGAGAG-
TAATATGTCAACG TTATTAGAAA GAGCTG-
TAGA AGCACTACAA GGAGAAAAAC GATAT-
TATAGTGATCCTCGA TTTCTCAATC
TCTGGCTTAA ATTAGGGCGT TTATGCAATG
AGCCTTTGGATATGTACAGT TACTTGCACA
ACCAAGGGAT TGGTGTTTCA CTTGCTCAGT
TCTATATCTCATGGGCAGAA GAATATGAAG
CTAGAGAAAA CTTTAGGAAA GCAGATGCGA
TATTTCAGGAAGGGATTCAA CAGAAGGCTG
AACCACTAGA AAGACTACAG TCCCAGCACC
GACAATTCCAAGCTCGAGTG TCTCGGCAAA
CTCTGTTGGC ACTTGAGAAA GAAGAAGAGG
AGGAAGTTTTTGAGTCTTCT GTACCACAAC
GAAGCACACT AGCTGAACTA AAGAGCAAAG
GGAAAAAGACAGCAAGAGCT CCAATCATCC
GTGTAGGAGG TGCTCTCAAG GCTCCAAGCC
AGAACAGAGG ACTCCAAAAT CCATTTCCTC
AACAGATGCA AAATAATAGT AGAATTACTG
TTTTTGATGA AAATGCTGAT GAGGCTTCTA
CAGCAGAGTT GTCTAAGCCT ACAGTCCAGC
CATGGATAGC ACCCCCCATG CCCAGGGCCA
AAGAGAATGA GCTGCAAGCA GGCCCTTGGA
ACACAGGCAGGTCCTTGGAA CACAGGCCTC
GTGGCAATAC AGCTTCACTG ATAGCTGTAC
CCGCTGTGCTTCCCAGTTTC ACTCCATATG
TGGAAGAGAC TGCACAACAG CCAGTTATGA
CACCATGTAAAATTGAACCT AGTATAAACC
ACATCCTAAG CACCAGAAG CCTGGAAAGG
AAGAAGGAGATCCTCTACAA AGGGTTCAGA
GCCATCAGCA AGCATCTGAG GAGAAGAAAG
AGAAGATGATGTATTGTAAG GAGAAGATTT
ATGCAGGAGT AGGGGAATTC TCCTTTGAAG
AAATTCGGGCTGAAGTTTTC CGGAAGAAAT
TAAAAGAGCA AAGGGAAGCC GAGCTATTGA
CCAGTGCAGAGAAGAGAGCA GAAATGCAGA
AACAGATTGA AGAGATGGAG AAGAAGCTAA
AAGAAATCCAAACTACTCAG CAAGAAAGAA
CAGGTGATCA GCAAGAAGAG ACGATGCCTA
CAAAGGAGACAACTAAACTG CAAATTGCTT
CCGAGTCTCA GAAAATACCA GGAATGACTC
TATCCAGTTCTGTTTGTCAA GTAAACTGTT
GTGCCAGAGA AACTTCACTT GCGGAGAACA
TTTGGCAGGA ACAACCTCAT TCTAAAGGTC
CCAGTGTACC TTTCTCCATT TTTGATGAGT
TTCTTCTTTCAGAAAAGAAG AACAAAAGTC
CTCCTGCAGA TCCCCCACGA GTTTTAGCTC
AACGAAGACCCCTTGCAGTT CTCAAAACCT
CAGAAAGCAT CACCTCAAAT GAAGATGTGT
CTCCAGATGTTTGTGATGAA TTTACAGGAA
TTGAACCCTT GAGCGAGGAT GCCATTATCA
CAGGCTTCAGAAATGTAACA ATTTGTCCTA
ACCCAGAAGA CACTTGTGAC TTTGCCAGAG
CAGCTCGTTTTGTATCCACT CCTTTTCATG
AGATAATGTC CTTGAAGGAT CTCCCTTCTG
ATCCTGAGAGACTGTTACCG GAAGAAGATC
TAGATGTAAA GACCTCTGAG GACCAGCAGA
CAGCTTGTGGCACTATCTAC AGTCAGACTC
TCAGCATCAA GAAGCTGAGC CCAATTATTG
AAGACAGTCGTGAAGCCACA CACTCCTCTG
GCTTCTCTGG TTCTTCTGCC TCGGTTGCAA
GCACCTCCTCCATCAAATGT CTTCAAATTC
CTGAGAAACT AGAACTTACT AATGAGACTT
CAGAAAACCCTACTCAGTCA CCATGGTGTT
CACAGTATCG CAGACAGCTA CTGAAGTCCC
TACCAGAGTTAAGTGCCTCT GCAGAGTTGT
GTATAGAAGA CAGACCAATG CCTAAGTTGG
AAATTGAGAAGGAAATTGAA TTAGGTAATG
AGGATTACTG CATTAAACGA GAATACCTAA
TATGTGAAGATTACAAGTTA TTCTGGGTGG
CGCCAAGAAA CTCTGCAGAA TTAACAGTAA
TAAAGGTATCTTCTCAACCT GTCCCATGGG
ACTTTTATAT CAACCTCAAG TTAAAGGAAC
GTTTAAATGAAGATTTTGAT CATTTTTGCA
GCTGTTATCA ATATCAAGAT GGCTGTATTG
TTTGGCACCAATATATAAAC TGCTTCACCC
TTCAGGATCT TCTCCAACAC AGTGAATATA
TTACCCATGA AATAACAGTG TTGATTATTT
ATAACCTTTT GACAATAGTG GAGATGCTAC
ACAAAGCAGAAATAGTCCAT GGTGACTTGA
GTCCAAGGTG TCTGATTCTC AGAAACAGAA
TCCACGATCCCTATGATTGT AACAAGAACA
ATCAAGCTTT GAAGATAGTG GACTTTTCCT
ACAGTGTTGACCTTAGGGTG CAGCTGGATG
TTTTTACCCT CAGCGGCTTT CGGACTGTAC
AGATCCTGGAAGGACAAAAG ATCCTGGCTA
ACTGTTCTTC TCCCTACCAG GTAGACCTGT
TTGGTATAGCAGATTTAGCA CATTTACTAT TGT-
TCAAGGA ACACCTACAG GTCTTCTGGG
ATGGGTCCTTCTGGAAACTT AGCCAAAATA
TTTCTGAGCT AAAAGATGGT GAATTGTGGA
ATAAATTCTTTGTGCGGATT CTGAATGCCA

ATGATGAGGC CACAGTGTCT GTTCTTGGGG AGCTTGCAGCAAAAATGAAT GGGGTTTTTG ACACTACATT CCAAAGTCAC CTGAACAAGG CCTTATGGAAGGTAGGGAAG TTAACTAGTC CTGGGGCTTT GCTCTTTCAG TGAGCTAGGC AATCAAGTCTCACAGATTGC TGCCTCAGAG CAATGGTTGT ATTGTGGAAC ACTGAAACTG TATGTGCTGTAATTTAATTT AGGACACATT TAGATGCACT ACCGTTGCTG TTCTACTTTT TGGTACAGGTATATTTTGAC GTCCTGATAT TTTTTATACA GTGATATACT TACTCCTGGC CTTGTCTAACTTTTGTGAAA AACTATTTTA TTCTAAACAG AATCATTACN AATGGTTACC TTGTTATTTAACCATTTGTT CTCTACTTTT CCCCGTACTT TTCCCATTTG TAATTTGTTA AAT- GTTCTCTTATGATCACC ATGTATTTTG TAAATAATAA AATAGTATCT GTTAAAAAAA AAAAAAAAAAAAAA.

EXAMPLE II

Identification of Two Kinetochore Kinases That are Related to Yeast BUB1 Checkpoint Kinase To verify that a human BUB1 kinase had been isolated in the two hybrid screen, the complete 3.9 kb cDNA was isolated by RT-PCR using ds cDNA from human K562 erythroleukemic cells. DNA sequence analysis showed that the similarity with the yeast kinase extended beyond the C-terminal kinase domain. The overall similarity was approximately 42% with 21% identity. This similarity strongly suggests that a human BUB1 homolog has been isolated.

Figure 3:
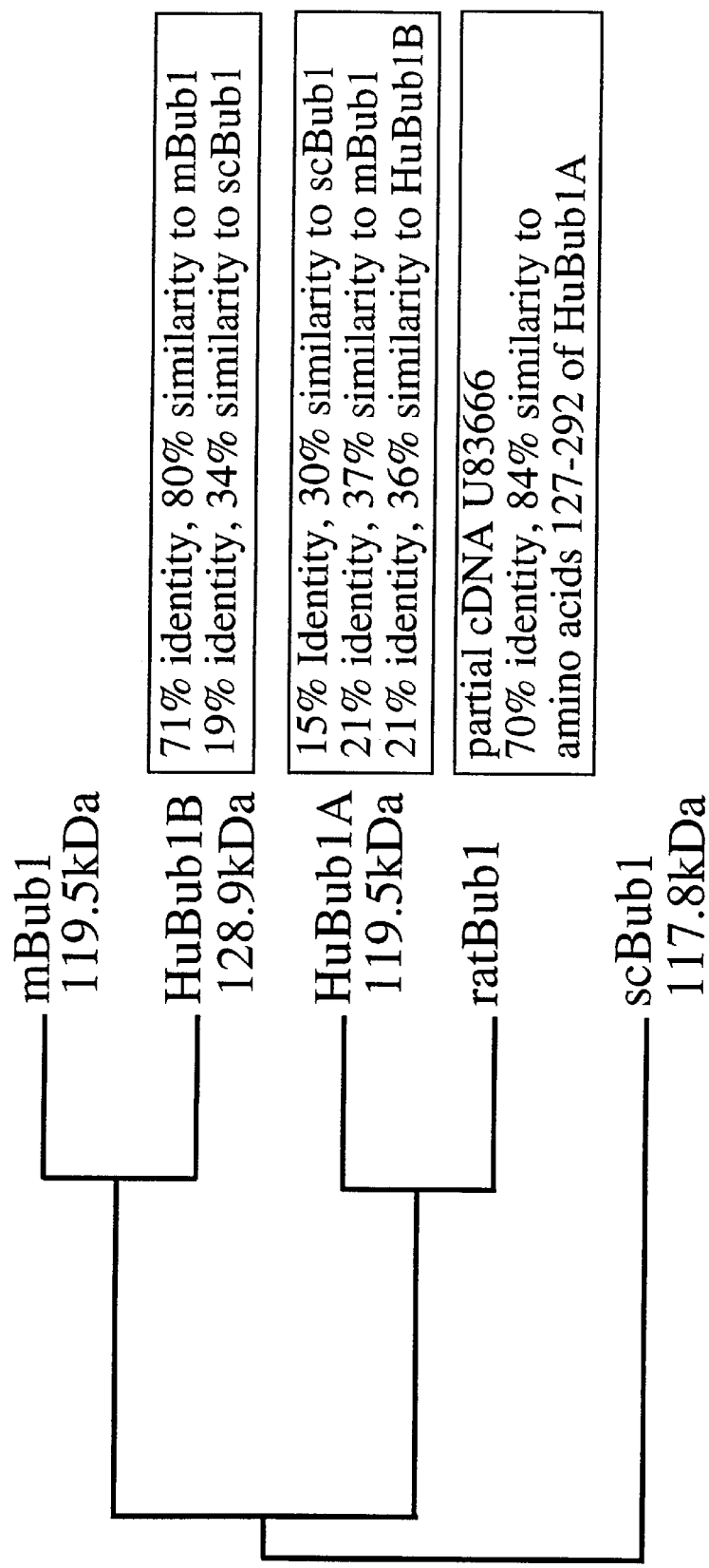
FIG. 3 is a dendrogram depicting the relatedness of BUB1 kinases from evolutionarily divergent species. The level of similarity shared between huBUB1A and huBUB1B was only slightly higher than their similarity to yeast BUb1. The low degree of similarity between these two human kinases indicate that they are encoded by separate genes.

Direct comparison of the primary amino acid sequences of yeast, mouse (30) and the human BUB1 kinases revealed that the human BUB1A kinase exhibited as much similarity with the yeast kinase as it did with the mouse kinase. Likewise, mouse BUB1 did not exhibit a greater degree of similarity with huBUB1A than with yeast BUB1 (FIG. 3). However, mouse BUB1 was found to be greater than 90% identical to human BUB1B cloned in this laboratory. The foregoing results indicate that huBUB1A, an interactor of CENP-E, is not the human homolog of mouse BUB1. More significantly, huBUB1B was independently isolated in a yeast two-hybrid screen wherein the kinetochore binding domain of CENP-F was used as bait. The specificity of the interactions of the two huBUB1 proteins was examined the results show that hUBUB1A interacts only with CENP-E but not CENP-F. Conversely, huBUB1B interacts with CENP-F and not with CENP-E. The full-length huBUB1B cDNA has been isolated and the complete sequence has been obtained. HuBUB1B has an 80 amino acid extension at its amino-terminus as compared with the mouse BUB1. This difference is due to the fact that the reported mouse BUB1 cDNA is incomplete. A comparison between huBUB1A and huBUB1B shows 24% identity and 49% similarity. Additionally, huBUB1A is predicted to be 8kDa smaller than huBUB1B kinase. The results presented herein show that two human BUB1 kinases have been isolated using functional screens which rely on interactions with known kinetochore proteins. The nucleic acid sequence of huBUB1B is set forth below as Sequence I.D. No. 3. It appears that human kinetochores are even more complex than suspected as there are at least two checkpoint kinases that may monitor different aspects of kinetochore functions. Given that there is a human homolog of the mouse BUB1, it is very surprising that a monoclonal antibody used in the mouse studies did not recognize the human protein. Sequence I.D. No. 3:

GGTGGTATTCGAATCGGCGGCGGCT-TCTAGTTTGCGGTTCAGGTTTGGCCGCTGCCG GCCAGCGTCCTCTGGCCATGGACAC-CCCGGAAAATGTCCTTCAGATGCT-TGAAGCCCACATGC AGAGCTACAAGGGCAAT-GACCCTCTTGGTGAATGGGAAAGATACATA CAGTGGGTAGAAGAG AATTTTCCT-GAGAATAAAGAATACTTGATAACTTTAC-TAGAACATTTAATGAAGGAATTTTTA GATAA-GAAGAAATACCACAATGACCCAAGATTCATC AGTTATTGTTTA
AAATTTGCTGAGTACA ACAGTGACCTCCAT-CAATTTTTTGAGTTTCTGTACAAC-CATGGGATTGGAACCCTGTCATCCC CTCTGTA-CATTGCCTGGGCGGGGCATCTGGAAGCCCA AGGAGAGCTGCAGCATGCCAGTGCTG TCCT-TCAGAGAGGAATTCAAAACCAGGCT-GAACCCAGAGAGTTCCTGCAACAACAATACAG GTTATTTCAGACACGCCTCACTGAAAC-CCATTTGCCAGCTCAAGCTAGAACCTCA-GAACCTCT GCATAATGTTCAGGTTTTAAAT-CAAATGATAACATCAAAATCAAATCCAGGA
AATAACATGGC CTGCATTTCTAAGAAT-CAGGGTTCAGAGCTTTCTGGAGTGATATCTT CAGCTTGTGATAAAGA GTCAAATATGGAAC-GAAGAGTGATCACGATTTCTAAATCA-GAATATTCTGTGCACTCATCTTTG GCATC-CAAAGTTGATGTTGAGCAGGTTGTTATGTAT TGCAAGGAGAA
GCTTATTCGTGGGGA ATCAGAATTTTC-CTTTGAAGAATTGAGAGCCCAGAAATA-CAATCAACGGAGAAAGCATGAGC AATGGG-TAAATGAAGACAGACATTATATGAAAAGGA AAGAAGCAA
ATGCTTTTGAAGAACA GCTATTAAAACA-GAAAATGGATGAACTTCATAAGAAGTTG-CATCAGGTGGTGGAGACATCCCA TGAGGATCT-GCCCGCTTCCCAGGAAAGGTCCGAGGTTA ATCCAGCAC
GTATGGGGCCAAGTG TAGGCTCCCAGCAG-GAACTGAGAGCGCCATGTCTTCCAG-TAACCTATCAGCAGACACCAGTG AACATG-GAAAAGAACCCAAGAGAGGCACCTCCTGT TGTTCCTCCTTT
GGCAAATGCTATTTCT GCAGCTTTGGTGTC-CCCAGCCACCAGCCAGAGCATTGCTC-CTCCTGTTCCTTTGAAAGCCCAG ACAGTAA-CAGACTC
CATGTTTGCAGTGGCCAGCAAAGAT-GCTGGATGTGTGAATAAGAGTAC TCATGAAT-TCAAGCCACAGAGTGGAGCAGAGAT-CAAAGAAGGGTGTGAAACACATAAGGTT GCCAACACAAGTTCTTTTCACACAACTC-CAAACACATCACTGGGAATGGTTCAG-GCAACGCC ATCCAAAGTGCACCCATCAC-CCACCGTGCACACAAAAGAAGCATTAGGT
TTCATCATGAATAT GTTTCAGGCTCCTACACT-TCCTGATATTTCTGATGACAAAGAT-GAATGGCAATCTCTAGATCAA AATGAAGATG-CATTTGAAGCCCAGTTTCAAAAAAATGTAA GGTCATCTGGGGCTTGGGGAGT CAATAAGAT-CATCTCTTCTTTGTCATCTGCTTTTCAT-GTGTTTGAAGATGGAAACAAAGAAAA TTATG-GATTACCACAGCCTAAAAATAAACCCACA GGAGCCAGGACCT
TTGGAGAACGCTCTG TCAGCAGACTTCCT-TCAAAACCAAAGGAGGAAGTGCCTCAT-GCTGAAGAGTTTTTGGATGAC TCAACTGTAT-

GCGGTATTCGCTGCAACAAAACCCTGGCAC
CCAGTCC
TAAGAGCCCAGGAGAC TTCACATCTGCTGCA-
CAACTTGCGTCTACACCATTCCA-
CAAGCTTCCAGTGGAGTCAGTGCAC ATTTTA-
GAAGATAAAGAAAATGTGGTAGCAAAACAG
TGTACCCAGGCGAC
TTTGGATTCTTG TGAGGAAAACATGGTGGT-
GCCTTCAAGGGATGGAAAATTCAGTC-
CAATTCAAGAGAAAAGCC CAAAACAGGCCT-
TGTCGTCTCACATGTATTCAGCATCCTTACTT
CGTCTGAGCCAGCCTGCTG CAGGTGGGG-
TACTTACCTGTGAGGCAGAGTTGGGCGT-
TGAGGCTTGCAGACTCACAGACACT GACGCT-
GCCATTGCAGAAGATCCACCAGGATCCGCTG
CCATTGCAGAAGATC
CACCAGATGC TATTGCTGGGCTCCAA-
GAGAATGGATGCAGATGAGTTCACTTGG-
GACTCTGTGATGCTCCAAA CTTCATTGTTGG-
GAACCCATGGGATGATAAGCTGATTTTCAA
ACTTTTATCTG
GGCTTTCTAAA CCAGTGAGTTCCTATC-
CAAATACTTTTGAATGGCAATGTAAACT-
TCCAGCCATCAAGCCCAAG ACTGAATTTCAAT-
TGGGTTCTAAGCTGGTCTATGTCCATCACCT
TCTTGGAGAAGGAGCCTTT GCCCAGGTGTAC-
GAAGCTACCCAGGGAGATCTGAATGAT-
GCTAAAAATAAACAGAAATTTGT TTTAAAG-
GTCCAAAAGCCTGCCAACCCCTGGGAATTCT
ACATTGGGACCCA
GTTGATGGAAA GACTAkAGCCATCTATCGAG-
CACATGTTTATGAAGTTCTATTCTGC-
CCACTTATTCCAGAATG GCAGTGTATTAGTAG-
GAGAGCTCTACAGCTATGGAACATTATTAAA
TGCCATTAAC
CTCTATA AAAATACCCCTGAAAAACTGATGC-
CTCAAGGTCTTGTCATCTCTTTTGCTAT-
GAGAATGCTTT ACATGATTGAGCAAGTGCAT-
GACTGTGAAATCATTCATGGAGACATTAAAC
CAGACAATTTC ATACTTGGAAACGGATTTTTG-
GAACAGGATGATGAAGATGATTTATCT-
GCTGGCTTGGCACTG ATTGACCTGGGTCA-
GAGTATAGATATGAAACTTTTTCCAAAAGG
AACTATA
TTCACAGCAAAG TGTGAAACATCTC-
CTTTTCAGTGTGTTGAGATGCTCAGCAA-
CAAACCATGGAACTACCAGAT CGAT-
TACTTTGGGGTGCTGCAACAGTATATTGCAT
GCTCTTTGGCACTTACATG
AAAGTGAAA AATGAAGGAGGACAGTG-
TAAGCCTGAAGGTCTTTTAGAAGGCT-
TCCTCATTTGGATATGTG GAAT-
GAATTTTTTCATGTTATGTTGAATATTCCAGA
TTGTCATCATCTTCCATCT
TTGGATTTGT TAAGGCAAAAGCTCAAGAAAG-
TATTTCAACAACACTATACTAACAA-
GATTAGGGCCCTACGT AATAGGCTAATTG-
TACTGCTCTTAGAATGTAAGCGTTCACGAAA
TAAAATTTGGATATAGA CAGTCCTTAAAAAT-
CAAAAAAAAAA.

EXAMPLE III

Characterization of KUBUB1A

Figures 5A, 5B:
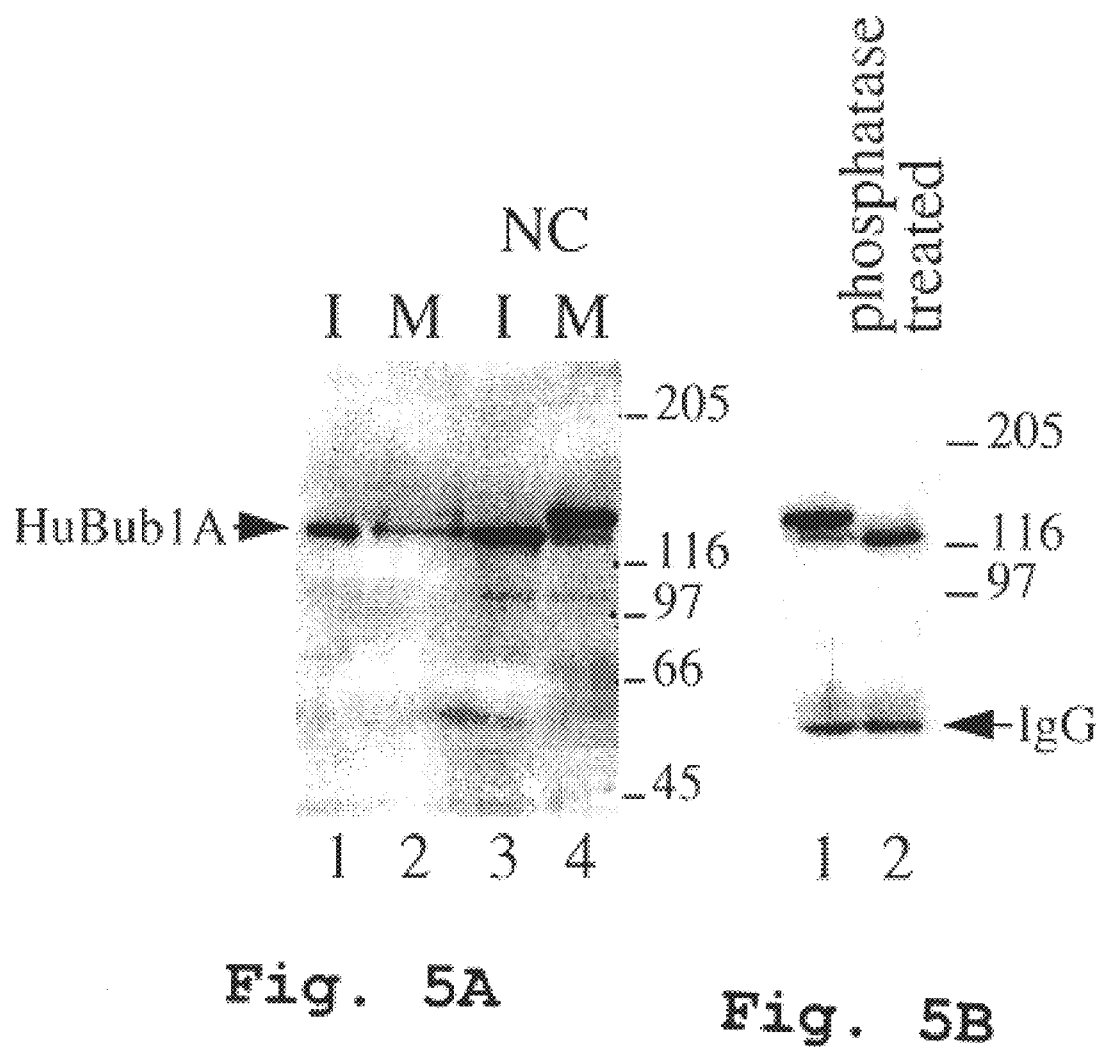
FIGS. 5A and 5B are a series of blots showing that huBUB1A is hyperphosphorylated in mitotically blocked cells.

Rat and rabbit polyclonal antibodies were raised against a unique segment of huBUB1A that did not share strong sequence similarities with huBUB1B/mouseBUB1. Sera were passed over a huBUB1A column and after extensive washing, antibodies were eluted with low pH, neutralized and concentrated. Immunoblots of Hela lysates using affinity-purified antibodies revealed a single band that migrated close to its calculated mass of 119 kDa (FIG. 4A, lane 1). Cell synchronization experiments (double thymidine block and centrifugal elutriation ) showed that while huBUB1A was detected throughout the cell cycle, levels of the protein peaked during G2 and M (FIG. 4C, lane 5). This pattern was very similar to that previously described for CENP-E and CENP-F (48, 50). A shift in huBUB1A mobility was observed in a pure population of mitotic cells that were obtained by mechanical shakeoff (FIG. 4C, lane 8.) It appears that huBUB1A was completely converted to the slower migrating form when cells were blocked in mitosis with nocodazole (FIG. 4B, lane 1 vs. lane 2). However, the modification was lost when cells were released from the block and allowed to enter G1 (FIG. 4B, compare lane 2 to lane 6). Comparison of the migration of huBUB1A between nocodazole-treated interphase and mitotic cells showed that the modification only occurred in mitotic cells (FIG. 5A; lane 3 vs lane 4) and was not simply a drug-induced artifact. As phosphatase treatment converted the slower form to the faster form that is found primarily in interphase, it appears that the protein is phosphorylated during mitosis (FIG. 5B lane 1 vs. lane 2). The combined data show that hUBUB1A is hyperphosphorylated in mitotically arrested cells.

Figure 6:
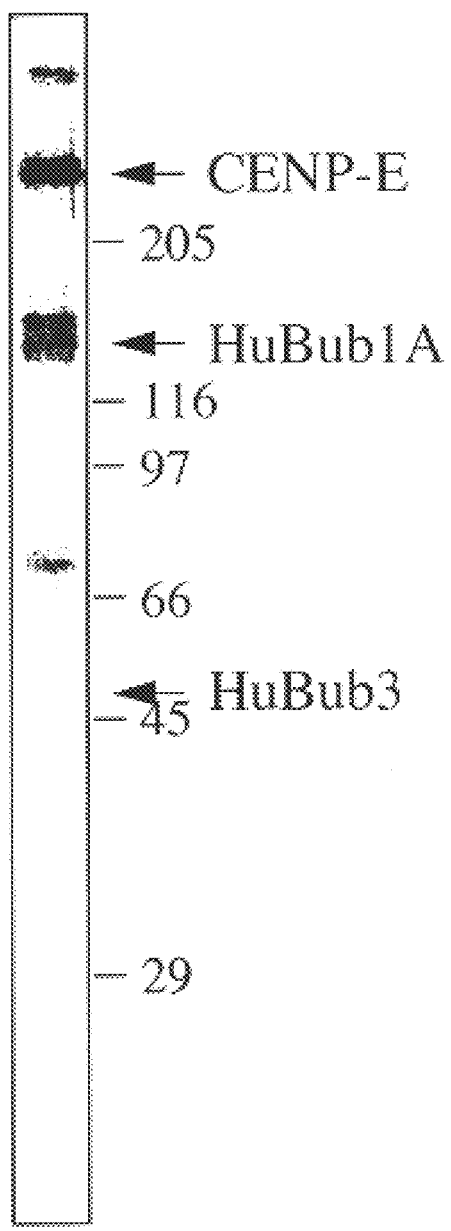
FIG. 6 is an autoradiogram of radiolabeled phosphoproteins that co-immunoprecipitate with CENP-E.
Figure 7A:
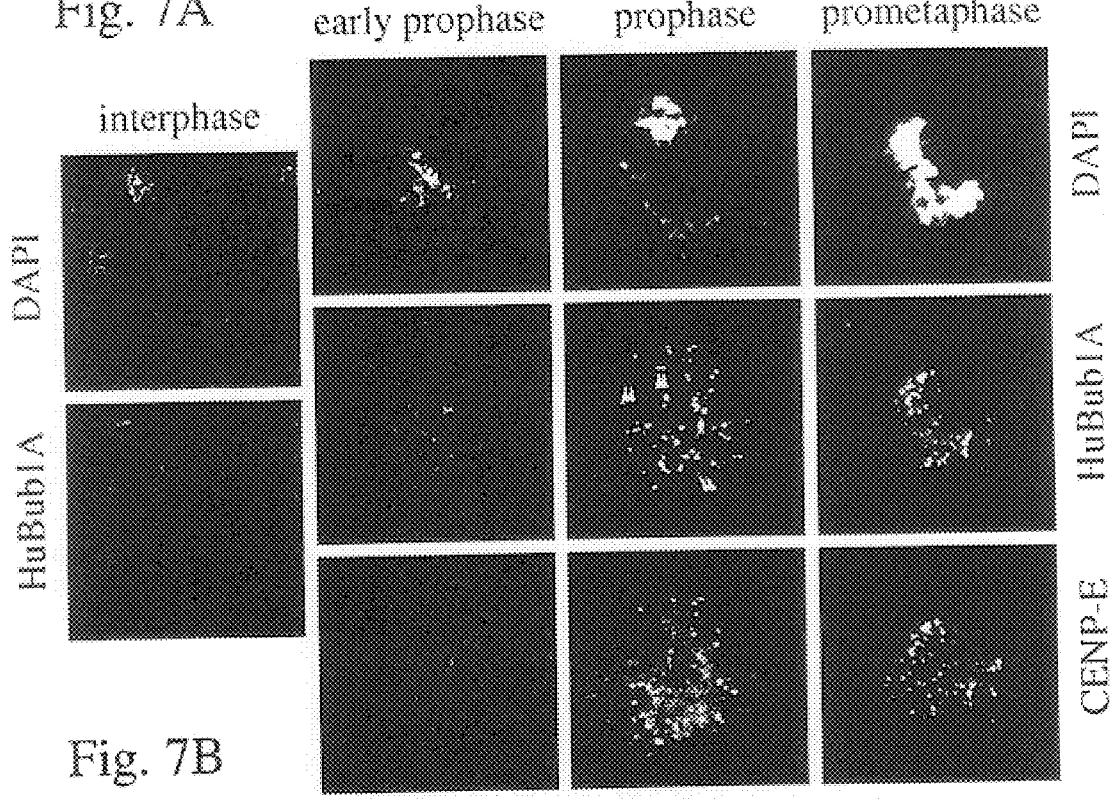
FIGS. 7A and 7B are a series of immunofluorescence micrographs showing the localization of huBUB1A and CENP-E in Hela cells. Hela cells were co-stained with rat anti-huBUB1A and rabbit anti-CENP-E antibodies and were visualized using FITC conjugated anti-rat and Texas Red conjugated anti-rabbit secondary antibodies. DNA and chromosomes were stained with DAPI and visualized by UV illumination.
Figure 7B:
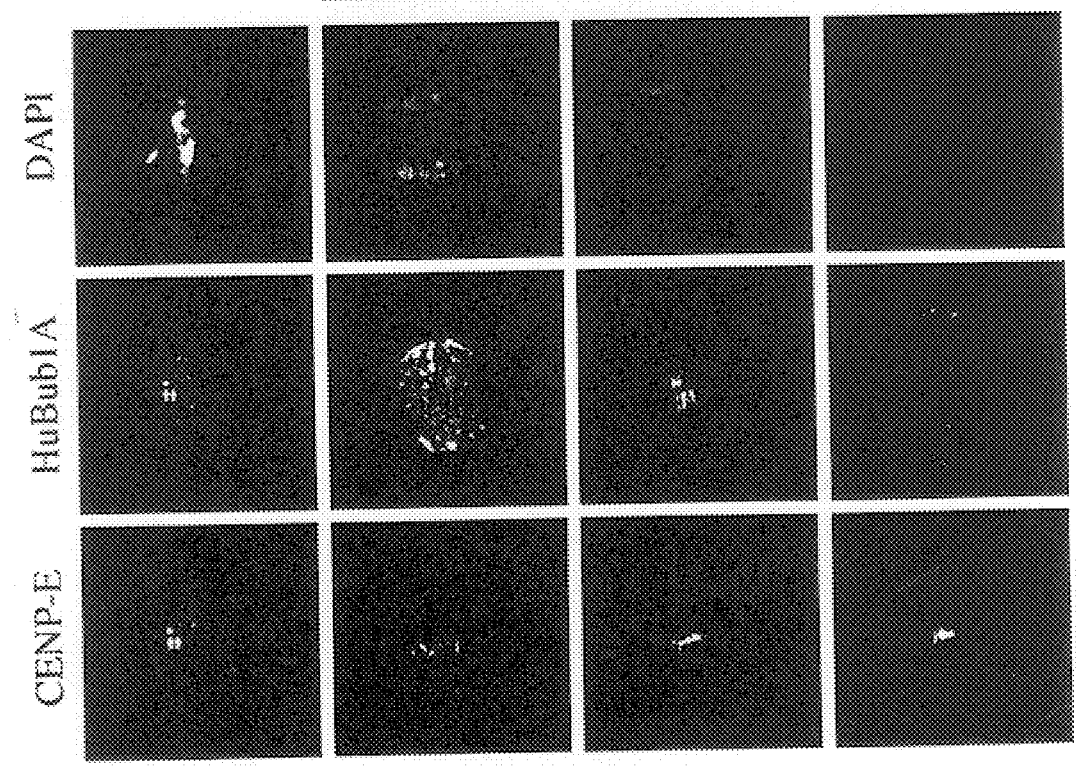

Further experiments demonstrated that huBUB1A co-immunoprecipitated with CENP-E in $^{32}$P-labeled mitotic extracts. The in vivo phosphorylated huBUB1A migrated as a smear that indicated that it was phosphorylated on multiple residues (FIG. 6). Phosphoamino acid analysis revealed that the P-ser and P-thr were the major phosphoamino acids (not shown). HuBUB1A is the first kinetochore protein that is known to be hyperphosphorylated and exhibit an induced kinase activity in response to a mitotic acrest. These phosphorylations include the checkpoint-sensitive 3F3/2 phosphoepitopes as well as phosphotyrosine. The CENP-E immunoprecipitates were found to contain additional phosphoproteins of approximately 70 kDa and approximately 40 kDa. In subsequent experiments using unlabeled samples, it was confirmed that the 40 kDa phosphoprotein is huBUB3 (described below) but the identity of the 70 kD phosphoprotein remains unknown. Consistent with the expression of huBUB1A throughout the cell cycle, immunofluorescence staining revealed that huBUB1A was detectable in the cytoplasm of all interphase cells (FIG. 7A, panel 1). While huBUB1A was found to accumulate in the cytoplasm, the interphase distribution of the mouse BUB1 (huBUB1B) was reported to be nuclear, although noticeable cell to cell variability in the intensity of nuclear staining was also observed (30). The difference in the interphase distribution of huBUB1A and mouse BUB1/huBUB1B further confirms that the antibodies used for these experiments are specific for huBUB1A. It is not clear at this time whether a mouse homolog of human BUB1A exists. Careful examination of many Hela and U2OS cells that were synchronized in the G2 phase of the cell cycle and double stained with huBUB1A and CENP-E antibodies showed that huBUB1A appeared at kinetochores sometime during prophase, slightly earlier than CENP-E (FIG. 7A, panel 2 vs. 3). HuBUB1B was determined to appear on kinetochores before huBUB1A (Jablonski et al., in press). As CENP-F can be detected at kinetochores before both huBUB1A and huBUB1B, the sequential appearance of these four proteins at the kinetochore is consistent with the hypothesis that there are discrete steps along the kinetochore assembly pathway. During prometaphase, huBUB1A is prominently localized at kinetochores. At metaphase, CENP-E and huBUB1A are co-localized at kinetochoreo as well as along kinetochore microtubules that extend towards the pole (FIG. 7A, panel 5). HuBUB1A was detectable at kinetochores in very early anaphase (notice the parallel rows of separated kinetochores, panel 2) but the staining intensity was severely diminished by mid-anaphase (FIG. 7B, panel 2 & 3). The only noticeable difference in the staining pattern between huBUB1A and CENP-E was that the midzone localization of huBUB1A at late anaphase was not coincident with CENP-E (FIG. 7B, panels 3 and 4). It is possible that at late stages of mitosis, CENP-E and huBUB1A interactions are lost.

EXAMPLE IV

Isolation of a Human BUB3 and its Interactions with huBUB1A and huBUB1B

In yeast, BUB1 and BUB3 form a complex and their presence is required for checkpoint-induced phosphorylation of MAD1p. Yeast BUB3 was isolated as a high-copy suppressor of an allele of BUB1. Loss of BUB3 produces spindle checkpoint defects that are virtually identical to those observed in BUB1 and BUB2 mutants. Thus, BUB3 may be a regulatory subunit that is important for some aspect of BUB1 function.

Using the yeast BUB3 protein sequence, the human EST database (tBLASTN) was screened and one candidate clone that contained a WD-40 motif was isolated. After obtaining the EST clone (from ATCC), additional DNA sequencing data showed that it was derived from the 3' end of an mRNA as it contained a consensus polyA site as well as a long stretch of polyA's. The EST cDNA was incomplete and full length cDNA was extended toward its 5' end by RACE. The complete cDNA was constructed by joining the 5' RACE product to the EST clone by PCR. Analysis of the DNA sequence obtained from the entire cDNA showed an open reading frame that encoded 348 amino acids with a calculated mass of 37.1 kDa. The size of this protein was very similar to yeast BUB3 and comparison of the primary sequence of these two proteins showed the 25% identity and 42% similarity. Further examination of the sequence by BEAUTY and BLOCKS revealed that the putative huBUB3 contained five WD-40 repeats. The nucleic acid sequence of BUB3 is set forth below as Sequence I.D. No. 5:

GGCACGTTCG GCACGAGGAA GCAAGGAGGC GGCGGCGGCC GAGCGAGTGG CGAGTAGTG-GAAACGTTGCT TCTGAGGGGA GCCCAAGATG ACCGGTTCTA ACGAGTTCAA GCTGAACCAGC-CACCCGAGG ATGGCATCTC CTCCGTGAAG TTCAGCCCCA ACACCTCCCA GTTCCTGCT-TGTCTCCTCCT GGGACACGTC CGTGCGTCTC TACGATGTGC CGGCCAACTC CATGCGGCT-CAAGTACCAGC ACACCGGCGC CGTCCTGGAC TGCGCCTTCT ACGATCCAAC GCATGCCTG-GAGTCGAGGAC TAGATCATCA ATTGAAAATG CATGATTTGA ACACTGATCA AGAAAATCTTGT-TGGGACCC ATGATGCCCC TATCAGATGT GTTGAATACT GTCCAGAAGT GAATGTGATG-GTCACTGGAA GTTGGGATCA GACAGTTAAA CTGTGGGATC CCAGAACTCC TTGTAAT-GCTGGGACCTTCT CTCAGCCTGA AAAGG-TATAT ACCCTCTCAG TGTCTGGAGA CCGGCT-G A T T G T C G G A A C A G C A G G C C G C A G AGTGTTGGTG TGGGACTTAC GGAACATGGG TTACGTGCAGCAGCGCAGGG AGTCCAGCCT GAAATACCAG ACTCGCTGCA TACGAGCGTT TCCAAACAAGCAGGGTTATG TATTAAGCTC TATTGAAGGC CGAGTGGCAG TTGAGTATTT GGACCCAAGCCCTGRGGTAC AGAAGAAGAA GTATGCCTTC AAATGTCACA GACTAAAAGA AAATAATATTGAGCAGATTT ACCCAGTCAA TGCCATTTCT TTTCACAATA TCCACAATAC ATTTGCCACAGGTGGTTCTG ATGGCTTTGT AAATATTTGG GATCCATTTA ACAAAAAGCG ACTGTGCCAATTCCATCGGT ACCCCACGAG CATCGCATCA CTTGCCTTCA GTAATGATGG GACTACGCTTGCAATAGCGT CATCATATAT GTATGAAATG GATGACACAG AACATCCTGA AGATGGTATCTTCATTCGCC AAGTGACAGA TGCAGAAACA AAACCCAAGT CACCATGTAC TTGACAAGATTTCATTTACT TAAGTGCCAT GTTGATGATA ATAAAACAAT TCGTACTCCC CAATGGTGGATTTATTACTA TTAAAGAAAC CAGGGAAAAT ATTAATTTTA ATATTATAAC AACCTGAAAATAATGGAAAA GAGGTTTTTG AATTTTTTTT TTTAAATAAA CACCTTCTTA AGT-GCAAAA.

Figure 8A:
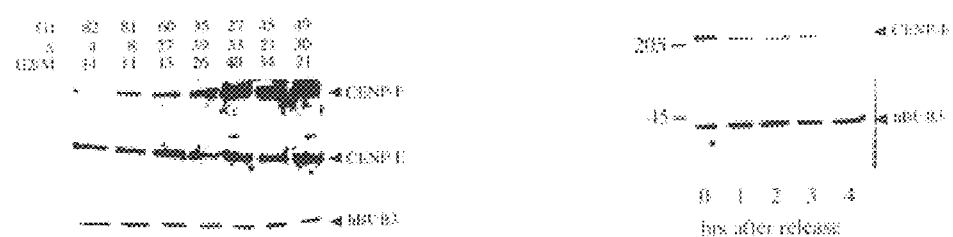
FIGS. 8A and 8B are an immunoblot and micrographs which reveal that huBUB3 is associated at kinetochores.
Figure 8B:
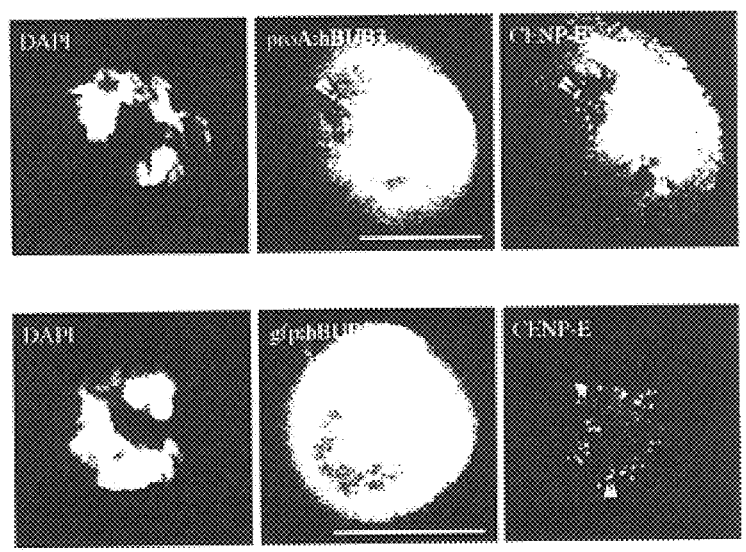

To confirm that human BUB3 had been isolated, several experiments were performed. Two independent methods were utilized to demonstrate that BUB3 was localized at kinetochores during mitosis. Affinity-purified huBUB3 antibodies produced a uniform nuclear staining of interphase cells (not shown). However, kinetochore staining was clearly apparent in mitotic cells (not shown). While these data were promising, the specificity of the affinity-purified antibodies was still a concern. Although immunoblots of whole cell lysates with these antibodies showed that they recognized a single band of the correct size (FIG. 8A), it was possible that the antibodies recognized some structural motif that maybe conserved amongst what superficially may appear as divergent WD-40 elements. To test whether huBUB3 is located at kinetochores, fusion proteins were constructed. Targeting of the heterologous protein, such as gfp (and protein A), to kinetochores by the BUB3 moiety was assessed. Hela cells were transfected with either gfp:huBUB3 or proA:huBUB3 constructs. Examination of transfected prometaphase and prophase cells clearly showed that both fusion proteins were localized at kinetochores (FIG. 8B).

Complex formation with huBUB1A was a second criteria used to establish the identity of huBUB3. HuBUB3 is a nuclear protein during interphase while its proposed subunit, huBUB1A, is distributed throughout the cytoplasm. The nuclear staining with huBUB3 antibodies appeared to be specific as western blot analysis of synchronized cell fractions showed that the huBUB3 antibody recognized a single protein of 40 kDa that was expressed uniformly throughout the cell cycle. It appears that huBUB1A and huBUB3 are separated from each other during interphase and they associate with each other only during mitosis.

To confirm that these proteins form a complex, huBUB1A and huBUB1B were separately immunoprecipitated from mitotic lysates and each immunoprecipitate probed with the same antibodies., respectively (FIG. 9 top panel, lanes 1 and 2). The bottom portion of the same filter was probed with huBUB3 (FIG. 9, bottom panel, lanes 1 and 2) Consistent with the data observed in yeast, huBUB1A and huBUB3 exist as a complex during mitosis. Examination of huBUB3 that was isolated from $^{32}$P-lysates showed that it was a phosphoprotein in interphase and mitosis. However, the phosphorylation was not noticeably altered when cells were blocked in mitosis (not shown). Although the majority of these phosphorylations are serines and threonines, they are not recognized by 3F3/2. The significance of these phosphorylations in mediating an association with huBUB1A is not known. However, hyperphosphorylation of huBUB1A does not appear to dramatically alter its interaction with huBUB3.

Similar experiments revealed that huBUB1B also formed a complex with huBUB3. As huBUB1A and huBUB1B do not form stable complexes with each other (Jablonski et al., in press), they must form distinct complexes with huBUB3.

EXAMPLE V

Kinase Activity of HuBUB1A and HuUB1B Varies According to Stage in the Cell Cycle Endogenous huBUB1A and huBUB1B kinase activites were assessed in cells that had been synchronized at different stages of the cell cycle. BUB1A and BUB1B were immunopreciptitated and kinase activity assessed.

FIG. 10A. shows an autoradiograph that reveals huBUB1A exhibits no detectable autokinase activity in cells that are synchronized at the G1, S and G2 stages of the cell cycle. Nevertheless, western blots of the identical samples show that huBUB1A is expressed at approximately equivalent levels throughout the cell cycle. Interestingly, huBUB1A autokinase activity was detected in cells that had entered mitosis. Furthermore, this kinase activity was significantly enhanced when cells are blocked in mitosis by microtubule inhibitors such as nocadozole. It is possible that huBUB1A kinase is activated in mitosis via hyperphosphorylation. Thus, it is possible that another kinase exists that specifically phosphorylates huBUB1A in mitosis and then activates its kinase activity.

In FIG. 10B, a similar analysis was performed on huBUB1B kinase using the identical set of extracts shown in 10A. HuBUB1B exhibited autokinase activity throughout the cell cycle and the level of kinase activity approximated the steady-state levels of the protein as determined by western blot. Thus, huBUB1B kinase activity differs in its regulation from that of huBUB1A. However, like huBUB1A, huBUB1B was also found to be hyperphosphorylated in mitotically blocked Hela cells.

EXAMPLE VI

HBUB1A Function is Essential for the Mitotic Checkpoint

Figure 11:
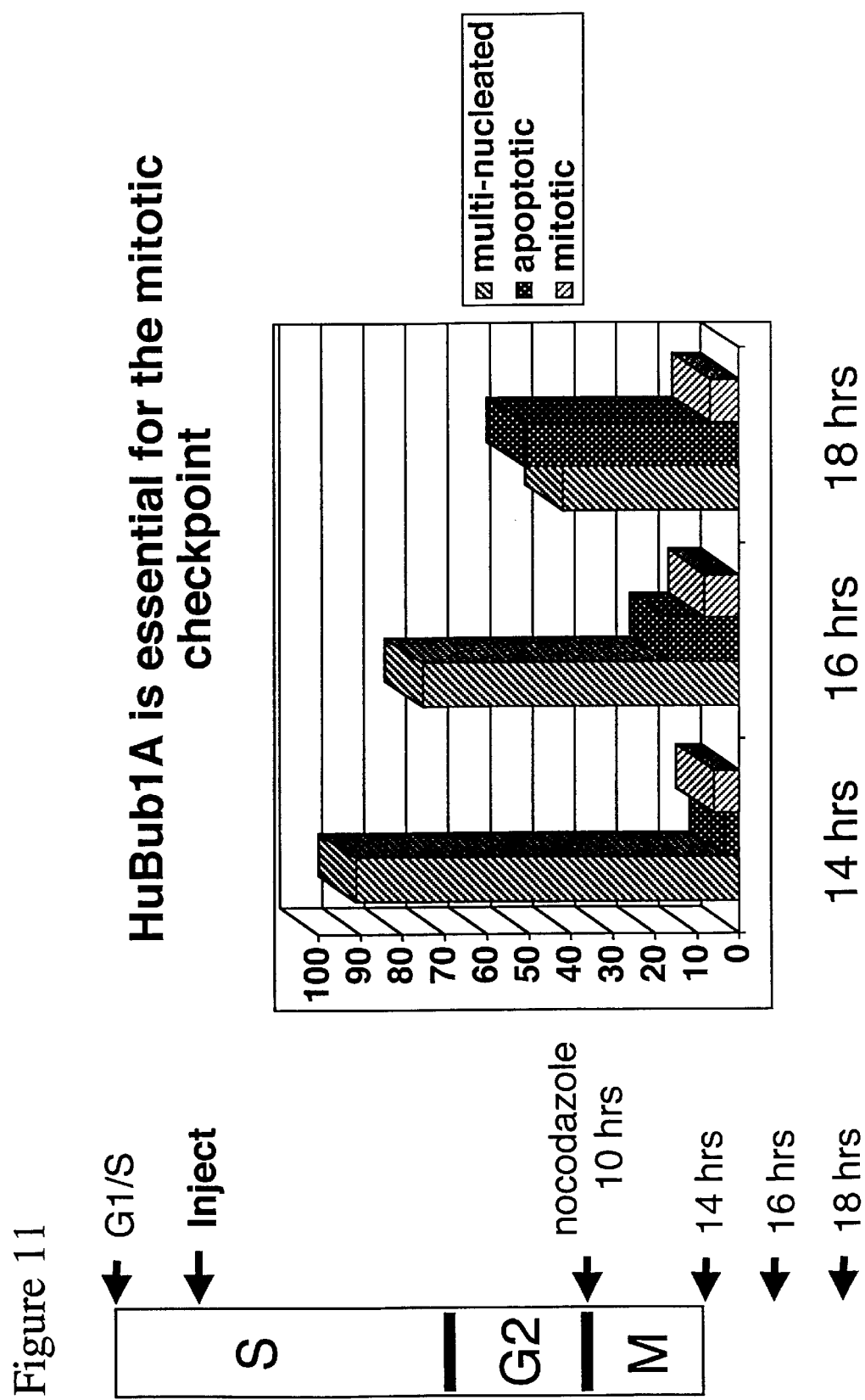
FIG. 11 is a histogram which shows the results of mitotic block experiments. The data show that cells injected with huBUB1A antibodies failed to arrest in mitosis in the presence of nocadozole and proceeded to undergo apoptosis as a result of premature exit from mitosis.

To directly examine whether huBUB1A is involved in the mitotic checkpoint pathway, Hela cells were microinjected with anti-huBUB1A antibodies to inhibit the activity of endogenous huBUB1A. Injected cells were then tested for their ability to remain arrested in mitosis when exposed to nocadozole. The data show that cells injected with huBUB1A antibodies failed to arrest in mitosis in the presence of nocadozole and proceeded to undergo apoptosis as a result of premature exit from mitosis. This demonstrates that huBUB1A plays an essential role in the mitotic checkpoint. See FIG. 11.

EXAMPLE VII

HUBUB1A is a Regular of the Cyclosome/APC Complex

Figure 12:
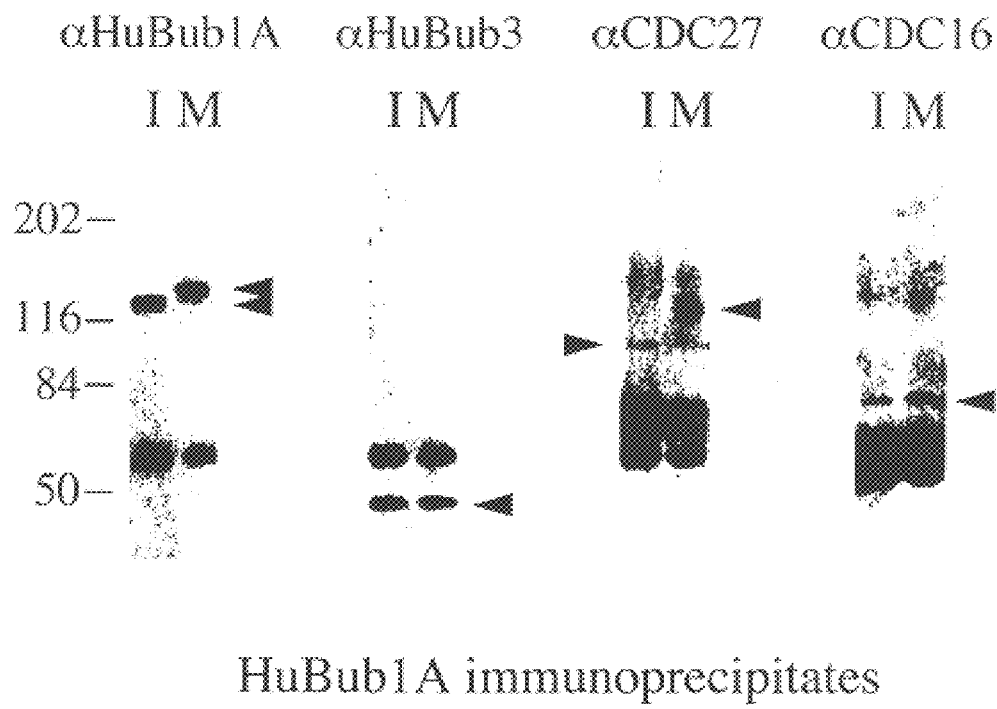
FIG. 12 shows western blots which reveal that huBUB1A physically associates with the cyclosome/APC complex. HuBUB1A was immunoprecipitated from Hela cells which were either in interphase, or mitotically arrested. The isolated immune complexes were then probed with antibodies to huBUB1A, huBUB3, CDC27, and CDC 16. The two subunits of the cyclosome/APC complex, CDC27 and CDC16 preferentially associate with huBUB1A in mitotically arrested cells.

We tested whether one of the mitotic checkpoint functions of huBUB1A was to inhibit the ubiquitin ligase activity of the cyclosome/APC complex. If this were the case, it is possible that huBUB1A physically associates with the cyclosome/APC complex. This hypothesis was tested by immunoprecipitating huBUB1A from interphase and mitotically arrested Hela cells and then probing the immunocomplexes with various antibodies. Western blots of the ip's show that approximately equivalent levels of huBUB1A were present in the interphase and mitotic samples and associated with huBUB3. When the same filter was probed with two subunits (cdc27 and cdc16) of the cyclosome/APC complex, they were found to preferentially associate with huBUB1A in the mitotically blocked cells. Arrowheads indicate position of the proteins that were identified with the antibodies used to probe the ip's. Gel filtration chromatography has been used to directly demonstrate that huBUB1A selectively associates with the cyclosome/APC complex (not only a subset of its subunits as shown by immunoprecipitations) only in mitosis. Thus, it appears that one mechanism of action of huBUB1A in the mitotic checkpoint is to directly inhibit cyclosome/APC functions. See FIG. 12.

EXAMPLE VIII

Methods for Screening Therapeutic Agents which Regulate Mitosis

HuBUB1A is expressed throughout the cell cycle but its protein kinase activity is only detected in cells that are in mitosis. HuBUB1A is therefore a mitosis-specific kinase. Functionally, we have demonstrated that huBUB1A kinase activity is essential for the mitotic checkpoint as overexpression of a kinase-defective mutant huBUB1A prevents cells from arresting in mitosis when exposed to anti-microtubule drugs.

Like endogenous huBUB1A, the mutant huBUB1A kinase can also be detected at kinetochores. Thus, huBUB1A is likely to be a component of the mitotic checkpoint at kinetochores that monitors the mechanical activities of the kinetochore as a mechanism to assess whether chromosomes have aligned or not. One function of huBUB1A is to initiate the mitotic checkpoint response when it detects kinetochroes of chromosomes that are not aligned properly with the spindle equator.

The signal emitted by the kinetochore that has not properly aligned with the spindle must be amplified and propagated throughout the cell to prevent premature exit from mitosis. HuBUB1A not only participates in initiating the mitotic checkpoint response, it also appears to amplify its own signal by activating the kinase activities of a global pool of huBUB1A. The final target of huBUB1A kinase appears to be the ubiquitin-ligase complex called the anaphase promoting complex. It has been shown that cell exit mitosis when the APC targets key proteins for ubiquitin mediated proteolysis. The mitotic checkpoint blocks or delays cells from exiting mitosis by blocking APC activity.

Several functional domains of huBUB1A have been identified which are important in the maintenance of mitotic checkpoint functions. These are as follows: 1) the domain involved in huBUB3 binding lies between amino acids; 194–466; 2) the domain that binds CENP-E lies between amino acids 408–546; 3) the domain by which huBUB1A binds the kinetochore lies between amino acids 1–466; and 4) the kinase domain of the protein lies within amino acids 644- to the carboxyl terminus.

The availability of BUB encoding nucleic acids, proteins, peptides and antibodies facilitates the identification of novel therapeutic agents which may be used to advantage in the treatment of malignancy.

To identify inhibitors of the BUB1A and BUB1B kinases of the invention, it is possible to use the nucleic acids of the invention to express the kinase domain of these proteins. Once purified, the peptides may be immobilized on a solid support. The immobilized peptides are then exposed to a combinatorial library of candidate compounds to identify those compounds which bind the kinase domain. Those compounds which bind the BUB kinase domain would be further characterized in in vitro kinase assays to assess inhibition autophosphorylation of BUB.

Alternatively, the candidate combinatorial compounds may be immobilized to a solid support. The support would then be exposed to full length BUB proteins. Those compounds that bound to the BUB(s) of the invention would then be assessed for either disruption of kinase activity or disruption of kinetochore binding.

We have defined the domains in huBUB1A that specify interactions with huBUB3, CENP-E and the kinetochore by transfecting these domains into tissue culture cells and then performing immunoprocipitation experiments to directly examine whether the transfected(l domain forms a stable complex with huBUB3 and CENP-E. For kinetochore binding activity, we visualize the subcellular localization of the transfected domains by conventional immunofluorescence microscopy. In all cases, candidate compounds can be added to transfected tissue culture cells or lysates derived therefrom to assess kinase or binding activity of the expressed domains in the presence of the candidate compounds. Once putative inhibitors are identified, they will be assessed for their ability to kinase activity of huBUB1A, for example, isolated from mitotic cells. Such inhibitors are likely to disrupt the mitotic checkpoint specified by huBUB1A, and therefore are likely to be efficacious in the treatment of disorders characterized by aberrant growth rates, such as cancer.

REFERENCES

1. Nicklas, R. B. and S. C. Ward 1994 Elements of error correction in mitosis: microtubule capture, release, and tension. J. Cell Biol. 126:1241–1253
2. Nicklas, R. B. 1997. How cells get the right chromosomes. Science 275:632–637
3. Murray, A. W. 1994 Cell Cycle Checkpoints. Curr. Opin. Cell Biol. 6:872–876
4. Gorbsky, G. J. 1995 Kinetochores, microtubules and the metaphase checkpoint Trends in Cell Biol. 5: 143–147
5. Rieder, C. L., A. Schultz, R. Cole, G. Sluder. 1994. Anaphase onset in vertebrate somatic cells is controlled by a checkpoint that monitors sister kinetochore attachment to the spinlde. J. Cell Biol. 127:1301–1310.
6. Inoue, S. and E. D. Salmon. 1995. Force generation by microtubule assembly/disassembly in mitosis and related movements. Mol. Biol. Cell. 6:1619–1640.
7. Yen, T. J. and B. T. Schaar. 1996. Kinetochore function: molecular motors, switches and gates. Curr. Opp. Cell Biol. 8:381–388.
8. Rieder, C. L., Cole, R. W., Khodjakov, A., G. Sluder. 1995. The checkpoint delaying anaphase in response to chromosome monoorientation is mediated by an inhibitory signal produced by unattached kinetochores. J. Cell Biol. 130:941–948.
9. King, R. W., R. J. Deshaies, J.-M. Peters, M. W. Kirschner. 1996. How proteolysis drives the cell cycle. Science 274:1652–1655.
10. Xiatong, L. and Nicklas, R. B. 1995. Mitotic forces control a cell-cycle checkpoint. Nature 373:630–632.
11. Cyert, M. S., Scherson, T., and Kirschener, M. W. 1988. Monoclonal antibodies specific for thiophosphorylated proteins recognize Xenopus MPF. Dev. Biol. 129:209–216.
12. Gorbsky, G. J., and Ricketts, W. A. 1993. Differential espression of a phosphoepitope at the kinetochores of moving chromosomes. J. Cell Biol 122:1311–1321.
13. Taagepera S. Campbell M S., Gorbsky G J. 1995. Cell-cycle-regulated localization of tyrosine and threonine phosphoepitopes at the kinetochores of mitotic chromosomes.Exp Cell Res 1:249–260.
14. Campbell, M. S. and Gorbsky, G. J. 1995. Microinjection of mitotic cells with the 3F3/2 antiphosphoepitope antibody delays the onset of anaphase. J. Cell Biol. 129:1195–1204.
15. Bernat, R. L., Borisy, G. G., Rothfield, N. F. and Earnshaw, W. C. 1990. Injection of anticentromere antibodies in interphase disrupts events required for chromosome movement at mitosis. J. Cell Biol. 111:1519–1533.
16. Yet, T. J., Compton, D. A., Wise, D., Zinkowski, R. P., Brinkley, B. B., Earnshaw, W. C., and Cleveland, D. W. 1991. CENP-E, a novel human centromere-associated protein required for progression ofrom metaphase to anaphase. EMBO J. 10:1245–1254.
17. Tomkiel, J., Cooke, C. A., Saitoh, H., Bernat, R. L., and Earnshaw, W. C. 1994. CENP-C is required from maintaining proper kinetochore size and for a timely transition to anaphase. J. Cell Biol. 125:531–545.
18. Nicklas;, R. B., Ward, S. C., and Gorbsky, G. J. 1995. Kinetochore chemistry is sensitive to tension and may link mitotic formces to a cell cycle checkpoint. J. Cell Biol. 130:929–939.
19. Hoyt, A. M., L/ Trotis., B. T. Roberts. 1991. S. cerevesiae genes requied for cell cycle arrest in response to loss of microtubule function. Cell 79:449–458.
20. Li, R. and A. W. Murray. 1991. Feedback control in budding yeast. Cell 66:519–531.
21. Hardwick, K. G. and A. W. Murray. 1995. Mad1p, a phosphoprotein component of the spindle assembly checkpoint in budding yeast. J. Cell Biol. 131:709–720.
22. Wells, W. A. and A. W. Murray. 1996. Aberrantlysegregating centromeres activate the spindle assembly checkpoint in budding yeast. J. Cell Biol. 133:75–84.
23. Pangilinan F, and F. Spencer. 1996. Abnormal kinetochore structure activates the spindle assembly checkpoint in budding yeast. Mol Biol Cell 8:1195–1208.
24. Wang Y, and D. J. Burke. 1995 Checkpoint genes required to delay cell division in response to nocodazole respond to impaired kinetochore function in the yeast Saccharomyces cerevisiae.Mol Cell Biol 15:6838–6844.
25. Roberts., R. T., K. A. Farr, M. A. Hoyt. 1994. The Saccharomyces cerevisiae checkpoint gene BUB1 encodes a novel protein kinase. Mol Biol Cell 14:8282–8291.
26. Hardwick K G, Weiss E, Luca F C, Winey M, Murray A W. 1996. Activation of the budding yeast spindle assembly checkpoint without mitotic spindle disruption Science 273:953–956.
27. Weiss E. and M. Winey. 1996. The Saccharomyces cerevisiae spindle pole body duplication gene MPS1 is part of a mitotic checkpoint. J. Cell Biol. 132:111–123.
28. Chen R H. Waters J C, Salmon E D, Murray A W. 1996. Association of spindle assembly checkpoint component XMAD2 with unattached kinetochores. Science 274:242–246.
29. Li Y, and Benezra R. 1996. Identification of a human mitotic checkpoint gene: hsMAD2. Science 274:246–248.
30. Taylor S S, and F. McKeon. 1997. Kinetochore localization of murine Bub1 is required for normal mitotic tiiaing and checkpoint response to spindle damage. Cell 89:727–735.

31. Minshull J, Sun H, Tonks N K, Murray A W. 1994. A MAP kinase-dependent spindle assembly checkpoint in Xenopus egg extracts.Cell 79:475–486.
32. Takenaka K, Gotoh Y, Nishida E. 1997. MAP kinase is require(d for the spindle assembly checkpoint but is dispensable for the normal M phase entry and exit in Xenopus egg cell cycle extracts. J. Cell Biol. 136:1091–1097.
33. Wang X M, Zhai Y, Ferrell J E Jr. 1997. A role for mitogen-activated protein kinase in the spindle assembly checkpoint in XTC cells. J Cell Biol 137:433–443.
34. Abrieu A, Lorca T, Labbe J C, Morin N, Keyse S, Doree M. 1996. MAP kinase does not inactivate, but rather prevents the cyclin degradation pathway from being turned on in Xenopus egg extracts. J. Cell Sci 109:239–246.
35. Holloway S L, Glotzer M, King R W, Murray A W. 1993. Anaphase is initiated by proteolysis rather than by the inactivation of maturation-promoting factor. Cell 73:1393–1402.
36. Peters J M, King R W, Hoog C, Kirschner M W. 1996. Identification of BIME as a subunit of the anaphase-promoting complex. Science 274(5290):1199–1201.
37. Tugendreich S, Tomkiel J, Earnshaw W, Hieter P. 1995. CDC27Hs colocalizes with CDC16Hs to the centrosome and mitotic spindle and is essential for the metaphase to anaphase transition. Cell 81:261–268.
38. Zachariae W, Shin T H, Galova M, Obermaier B, Nasmyth K. 1996. Identification of subunits of the anaphase-promoting complex of Saccharomyces cerevisiae. Science 274:1201–1204.
39. Yamashita Y M, Nakaseko Y, Samejima I, Kumada K, Yamada H, Michaelson D, Yanagida M. 1996. 20S cyclosome complex formation and proteolytic activity inhibited bit the cAMP/PKA pathway. Nature 384:276–279.
40. Irniger S, Piatti S, Michaelis C, Nasmyth K. 1995. Genes involved in sister chromatid separation are needed for B-type cyclin proteolysis in budding yeast.Cell 81:269–278.
41. Yamamoto A, Guacci V, Koshland. D. 1996. Pds1p, an inhibitor of anaphase in budding yeast, plays a critical role in the APC and checkpoint pathway(s). J Cell Biol 133:99–110.
42. Cohen-Fix O, Peters J M, Kirschner M W, Koshland D. 1996. Anaphase initiation in Saccharomyces cerevisiae is controlled by the APC-dependent degradation of the anaphase inhibitor Pds1p. Genes Dev 10:3081–3093.
43. Funabiki H, Yamano H, Kumada K, Nagao K, Hunt T, Yanagida M. 1996. Cut2 proteolysis required for sister-chronuatid seperation in fission yeast. Nature 381:438–441.
44. Funabiki H, Kumada K, Yanagida M. 1996. Fission yeast Cut1 and Cut2 are essential for sister chromatid separation, concentrate along the metaphase spindle and form large complexes. EMBO J 15:6617–6628.
45. He X, Patterson T E, Sazer S. 1997. The Schizosaccharomyces pombe spindle checkpoint protein mad2p blocks anaphase and genetically interacts with the anaphase-promoting complex. Proc Natl Acad Sci U S A. 94:7965–7970.
46. Wang Y, Burke D J. 1997. Cdc55p, the B-type regulatory subunit of protein phosphatase 2A, has multiple functions in mitosis and is required for the kinetochore/spindle checkpoint in Saccharomyces cerevisiae. Mol Cell Biol 17:620–626.
47. Minshull J, Straight A, Rudner A D, Dernburg A F, Belmont A, Murray A W. 1996. Protein phosphatase 2A regulates MPF activity and sister chromatid cohesion in budding yeast. Curr Biol. 6:1609–1620.
48. Sheay, W., S. Nelson, I. Martinez, T. H. Chu, S. Bhatia and R. Dornburg. 1993. Downstream insertion of the adenovirus tripartite leader sequence enhances expression in universal eukaryotic vectors. Biotechniques. 15:856–862.
49. McEwen, B. F., A. B. Heagle, Cassels, G. O., K. F. Buttle, C. L. Rieder. 1997. Kinetochore fiber inPtK1 cells and its implications for the mechanisms of chromosome congression and anaphase onset.
50. Pluta A F, Saitoh N, Goldberg I, Earnshaw W C. 1992. Identification of a subdomain of CENP-B that is necessary and sufficient for localization to the human centromere J. Cell Biol 116:1081–1093.
51. Heider, H., C. Hug, J. M. Lucocq. 1994. A 40 kDa myelin basic protein kinase, distinct from erkl and erk2 is activated in mitotic Hela cells. Eur. J. Biochem. 219:513–520.
52. Hartweil, L. H., T. A. Weinert. 1989. Checkpoint: controls that ensure the order of cell cycle events. Science 246:629–634.
53. Jablonski et al. 1998 hBUB1 and hBUBR1 kinases sequentially assemble onto kinetochore during prophase with hBUBR1 concentrating at the kinetochore plates in mitosis. Chromosoma, in press.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated double-stranded nucleic acid molecule which, upon denaturation, comprises SEQ ID NO: 1, said nucleic acid molecule comprising a sequence encoding a human BUB1A kinase about 120 amino acids in length, said encoded kinase comprising an amino terminal kinetochore targeting domain, a central α-helical coil domain and a carboxy terminal kinase domain.

2. The nucleic acid molecule of claim 1, which is DNA.

3. The DNA molecule of claim 2, which is a cDNA comprising a sequence approximately 3.9 kilobase pairs in length that encodes said human BUB1A kinase.

4. The DNA molecule of claim 2, which is a gene comprising introns and exons, the exons of said gene specifically hybridizing with the nucleic acid of SEQ ID NO 1, and said exons encoding said human BUB1A kinase protein.

5. An isolated RNA molecule transcribed from the nucleic acid of claim 1.

6. The nucleic acid molecule of claim 1, wherein said sequence encodes a human BUB1A kinase protein comprising an amino acid sequence selected from the group consisting of an amino acid sequence encoded by SEQ ID NO: 2 and amino acid sequences having greater than 95% identity with SEQ ID NO: 2, wherein said amino acid sequences having greater than 95% identity with SEQ ID NO: 2 display a BUB1A kinase activity.

7. The nucleic acid molecule of claim 6, which comprises SEQ ID NO 1.

8. An isolated nucleic acid molecule comprising a sequence selected from the group consisting of:
   a) SEQ ID NO: 1; and
   b) a sequence encoding a polypeptide of SEQ ID NO: 2.

9. An oligonucleotide between about 10 and about 200 nucleotides in length, which specifically hybridizes with a protein translation initiation site in a nucleotide sequence encoding amino acids of SEQ ID NO 2.

10. An isolated human BUB1A kinase protein, about 1012 amino acids in length comprising SEQ ID NO: 2, said encoded protein comprising an amino terminal kinetochore targeting domain, a central α-helical coil domain and a carboxy terminal kinase domain.

11. An isolated double-stranded nucleic acid molecule which, upon denaturation, comprises SEQ ID NO: 3, said nucleic acid molecule comprising a sequence encoding a human BUB1B kinase, said BUB1B kinase having affinity for kinetochore protein CENP-F.

12. The nucleic acid molecule of claim 11, which is DNA.

13. The DNA molecule of claim 15, which is a cDNA comprising a sequence approximately 3.8 kilobase pairs in length that encodes said human BUB1B kinase.

14. The DNA molecule of claim 12, which is a gene comprising introns and exons, the exons of said gene specifically hybridizing with the nucleic acid of SEQ ID NO 3, and said exons encoding said human BUB1B kinase protein.

15. An isolated RNA molecule transcribed from the nucleic acid of claim 11.

16. The nucleic acid molecule of claim 13, wherein said sequence encodes a human BUB1B kinase protein comprising an amino acid sequence selected from the group consisting of SEQ ID NO: 4 and amino acid sequences having greater than 95% identity with SEQ ID NO: 4, wherein said amino acid sequences having greater than 95% identity with SEQ ID NO: 4 display a BUB1B kinase activity.

17. The nucleic acid molecule of claim 16, which comprises SEQ ID NO 3.

18. An isolated nucleic acid molecule comprising a sequence selected from the group consisting of:
   a) SEQ ID NO: 3; and
   b) a sequence encoding a polypeptide of SEQ ID NO: 4.

19. An oligonucleotide between about 10 and about 200 nucleotides in length, which specifically hybridizes with a protein translation initiation site in a nucleotide sequence encoding amino acids of SEQ ID NO 4.

20. An isolated human BUB1B kinase protein, about 1200 amino acids in length comprising SEQ ID NO: 4, said encoded protein comprising a terminal kinetochore targeting domain, a central α-helical coil domain and a carboxy terminal kinase domain.

21. An isolated double-stranded nucleic acid molecule which, upon denaturation, comprises SEQ ID NO: 5, said nucleic acid molecule comprising a sequence encoding a human BUB3 protein about 348 amino acids in length, said BUB3 protein comprising five WD-40 repeat motifs and complexing with human BUB1A kinase.

22. The nucleic acid molecule of claim 21, which is DNA.

23. The DNA molecule of claim 22, which is a cDNA comprising a sequence approximately 1.3 kilobase pairs in length that encodes said human BUB3 protein.

24. The DNA molecule of claim 22, which is a gene comprising introns and exons, the exons of said gene specifically hybridizing with the nucleic acid of SEQ ID NO 5, and said exons encoding said human BUB3protein.

25. An isolated RNA molecule transcribed from the nucleic acid of claim 21.

26. An isolated nucleic acid molecule comprising a sequence selected from the group consisting of:
   a) SEQ ID NO: 5; and
   b) a sequence encoding a polypeptide of SEQ ID NO: 6.

27. An oligonucleotide between about 10 and about 200 nucleotides in length, which specifically hybridizes with a protein translation initiation site in a nucleotide sequence encoding amino acids of SEQ ID NO 6.

28. An isolated human BUB3 protein about 348 amino acids in length comprising SEQ ID NO: 6, said encoded protein complexing with human BUB1A kinase.

29. An antibody immunologically specific for the isolated protein of claim 28.

30. A method for identifying therapeutic agents which inhibit kinase activity of BUB1A protein comprising an amino acid sequence of SEQ ID NO: 2, said method comprising:
   a) providing a BUB1A polypeptide containing a kinase domain;
   b) exposing said peptide to candidate therapeutic agents and isolating those candidate therapeutic agents which bind to said BUB1A kinase domain; and
   c) performing an in vitro kinase assay to assess BUB kinase activity in the presence and absence of said candidate therapeutic agent that binds to said BUB1A polypeptide.

* * * * *

SEQUENCE LISTING

<160> NUMBER OF SEQ ID NOS: 13

<210> SEQ ID NO 1
<211> LENGTH: 3664
<212> TYPE: DNA
<213> ORGANISM: Homo sapiens
<220> FEATURE:
<221> NAME/KEY: misc_feature
<222> LOCATION: (3520)...(3521)
<223> OTHER INFORMATION: n = A, T, C, or G

<400> SEQUENCE: 1
gttagggagt cgtgtgcgtg ccttggtcgc ttctgtagct ccgagggcag gttgcggaag    60

```
aaagcccagg cggtctgtgg cccagaagaa aggcctgcag caggacgagg acctgagcca    120
ggaatgcagg atggcggcgg tgaaaaagga aggggggtgct ctgagtgaag ccatgtccct   180
ggagggagat gaatgggaac tgagtaaaga aaatgtacaa cctttaaggc aagggcggat    240
catgtccacg cttcagggag cactggcaca agaatctgcc tgtaacaata ctcttcagca    300
gcagaaacgg gcatttgaat atgaaattcg attttacact ggaaatgacc ctctggatgt    360
ttgggatagg tatatcagct ggacagagca gaactatcct caaggtggga aggagagtaa    420
tatgtcaacg ttattagaaa gagctgtaga agcactacaa ggagaaaaac gatattatag    480
tgatcctcga tttctcaatc tctggcttaa attagggcgt ttatgcaatg agcctttgga    540
tatgtacagt tacttgcaca accaagggat tggtgtttca cttgctcagt tctatatctc    600
atgggcagaa gaatatgaag ctagagaaaa ctttaggaaa gcagatgcga tatttcagga    660
agggattcaa cagaaggctg aaccactaga aagactacag tcccagcacc gacaattcca    720
agctcgagtg tctcggcaaa ctctgttggc acttgagaaa aagaagagg aggaagtttt     780 tgagtcttct gtaccacaac gaagcacact agctgaacta aagagcaaag ggaaaaagac    840
agcaagagct ccaatcatcc gtgtaggagg tgctctcaag gctccaagcc agaacagagg    900
actccaaaat ccatttcctc aacagatgca aaataatagt agaattactg ttttttgatga   960 aaatgctgat gaggcttcta cagcagagtt gtctaagcct acagtccagc catggatagc   1020
accccccatg cccagggcca aagagaatga gctgcaagca ggcccttgga acacaggcag   1080
gtccttggaa cacaggcctc gtggcaatac agcttcactg atagctgtac ccgctgtgct   1140
tcccagtttc actccatatg tggaagagac tgcacaacag ccagttatga caccatgtaa   1200
aattgaacct agtataaacc acatcctaag caccagaaag cctggaaagg aagaaggaga   1260
tcctctacaa agggttcaga gccatcagca agcatctgag gagaagaaag agaagatgat   1320
gtattgtaag gagaagattt atgcaggagt aggggaattc tcctttgaag aaattcgggc   1380
tgaagttttc cggaagaaat taaaagcaa agggaagcc gagctattga ccagtgcaga    1440
gaagagagca gaaatgcaga aacagattga agagatggag aagaagctaa aagaaatcca   1500
aactactcag caagaaagaa caggtgatca gcaagaagag acgatgccta caaaggagac   1560
aactaaactg caaattgctt ccgagtctca gaaaatacca ggaatgactc tatccagttc   1620
tgtttgtcaa gtaaactgtt gtgccagaga aacttcactt gcggagaaca tttggcagga   1680
acaacctcat tctaaaggtc ccagtgtacc tttctccatt tttgatgagt ttcttctttc   1740
agaaaagaag aacaaaagtc ctcctgcaga tcccccacga gttttagctc aacgaagacc   1800
ccttgcagtt ctcaaaacct cagaaagcat cacctcaaat gaagatgtgt ctccagatgt   1860
ttgtgatgaa tttacaggaa ttgaacccctt gagcgaggat gccattatca caggcttcag   1920
aaatgtaaca atttgtccta acccagaaga cacttgtgac tttgccagag cagctcgttt   1980
tgtatccact cctttttcatg agataatgtc cttgaaggat ctcccttctg atcctgagag   2040
actgttaccg gaagaagatc tagatgtaaa gacctctgag gaccagcaga cagcttgtgg   2100
cactatctac agtcagactc tcagcatcaa gaagctgagc ccaattattg aagacagtcg   2160
tgaagccaca cactcctctg gcttctctgg ttcttctgcc tcggttgcaa gcacctcctc   2220
catcaaatgt cttcaaattc ctgagaaact agaacttact aatgagactt cagaaaaccc   2280
tactcagtca ccatggtgtt cacagtatcg cagacagcta ctgaagtccc taccagagtt   2340
aagtgcctct gcagagttgt gtatagaaga cagaccaatg cctaagttgg aaattgagaa   2400
```

-continued

```
ggaaattgaa ttaggtaatg aggattactg cattaaacga gaatacctaa tatgtgaaga    2460
ttacaagtta ttctgggtgg cgccaagaaa ctctgcagaa ttaacagtaa taaggtatc    2520 ttctcaacct gtcccatggg acttttatat caacctcaag ttaaaggaac gtttaaatga    2580
agattttgat cattttgca gctgttatca atatcaagat ggctgtattg tttggcacca    2640
atatataaac tgcttcaccc ttcaggatct tctccaacac agtgaatata ttacccatga    2700
aataacagtg ttgattattt ataacctttt gacaatagtg gagatgctac acaaagcaga    2760
aatagtccat ggtgacttga gtccaaggtg tctgattctc agaaacagaa tccacgatcc    2820
ctatgattgt aacaagaaca atcaagcttt gaagatagtg gacttttcct acagtgttga    2880
ccttagggtg cagctggatg ttttaccct cagcggcttt cggactgtac agatcctgga    2940
aggacaaaag atcctggcta actgttcttc tccctaccag gtagacctgt ttggtatagc    3000
agatttagca catttactat tgttcaagga cacctacag gtcttctggg atgggtcctt    3060
ctggaaactt agccaaaata tttctgagct aaaagatggt gaattgtgga ataaattctt    3120
tgtgcggatt ctgaatgcca atgatgaggc cacagtgtct gttcttgggg agcttgcagc    3180
aaaaatgaat ggggtttttg acactacatt ccaaagtcac ctgaacaagg ccttatggaa    3240
ggtagggaag ttaactagtc ctggggcttt gctctttcag tgagctaggc aatcaagtct    3300
cacagattgc tgcctcagag caatggttgt attgtggaac actgaaactg tatgtgctgt    3360
aatttaattt aggacacatt tagatgcact accgttgctg ttctactttt tggtacaggt    3420
atattttgac gtcctgatat tttttataca gtgatatact tactcctggc cttgtctaac    3480
ttttgtgaaa aactattta ttctaaacag aatcattacn aatggttacc ttgttattta    3540
accatttgtt ctctactttt ccccgtactt ttcccatttg taatttgtta aatgttctct    3600
tatgatcacc atgtattttg taaataataa aatagtatct gttaaaaaaa aaaaaaaaa    3660 aaaa                                                                3664
```

<210> SEQ ID NO 2
<211> LENGTH: 1050
<212> TYPE: PRT
<213> ORGANISM: Homo sapiens

<400> SEQUENCE: 2

```
Met Ala Ala Val Lys Lys Glu Gly Gly Ala Leu Ser Glu Ala Met Ser
 1               5                  10                  15

Leu Glu Gly Asp Glu Trp Glu Leu Ser Lys Glu Asn Val Gln Pro Leu
                20                  25                  30

Arg Gln Gly Arg Ile Met Ser Thr Leu Gln Gly Ala Leu Ala Gln Glu
            35                  40                  45

Ser Ala Cys Asn Asn Thr Leu Gln Gln Gln Lys Arg Ala Phe Glu Tyr
        50                  55                  60

Glu Ile Arg Phe Tyr Thr Gly Asn Asp Pro Leu Asp Val Trp Asp Arg
 65                  70                  75                  80

Tyr Ile Ser Trp Thr Glu Gln Asn Tyr Pro Gln Gly Gly Lys Glu Ser
                85                  90                  95

Asn Met Ser Thr Leu Leu Glu Arg Ala Val Glu Ala Leu Gln Gly Glu
                100                 105                 110

Lys Arg Tyr Tyr Ser Asp Pro Arg Phe Leu Asn Leu Trp Leu Lys Leu
            115                 120                 125

Gly Arg Leu Cys Asn Glu Pro Leu Asp Met Tyr Ser Tyr Leu His Asn
        130                 135                 140
```

-continued

```
Gln Gly Ile Gly Val Ser Leu Ala Gln Phe Tyr Ile Ser Trp Ala Glu
145                 150                 155                 160
Glu Tyr Glu Ala Arg Glu Asn Phe Arg Lys Ala Asp Ala Ile Phe Gln
            165                 170                 175
Glu Gly Ile Gln Gln Lys Ala Glu Pro Leu Glu Arg Leu Gln Ser Gln
        180                 185                 190
His Arg Gln Phe Gln Ala Arg Val Ser Arg Gln Thr Leu Leu Ala Leu
    195                 200                 205
Glu Lys Glu Glu Glu Glu Val Phe Glu Ser Ser Val Pro Gln Arg
210                 215                 220
Ser Thr Leu Ala Glu Leu Lys Ser Lys Gly Lys Lys Thr Ala Arg Ala
225                 230                 235                 240
Pro Ile Ile Arg Val Gly Gly Ala Leu Lys Ala Pro Ser Gln Asn Arg
                245                 250                 255
Gly Leu Gln Asn Pro Phe Pro Gln Gln Met Gln Asn Asn Ser Arg Ile
            260                 265                 270
Thr Val Phe Asp Glu Asn Ala Asp Glu Ala Ser Thr Ala Glu Leu Ser
        275                 280                 285
Lys Pro Thr Val Gln Pro Trp Ile Ala Pro Met Pro Arg Ala Lys
    290                 295                 300
Glu Asn Glu Leu Gln Ala Gly Pro Trp Asn Thr Gly Arg Ser Leu Glu
305                 310                 315                 320
His Arg Pro Arg Gly Asn Thr Ala Ser Leu Ile Ala Val Pro Ala Val
                325                 330                 335
Leu Pro Ser Phe Thr Pro Tyr Val Glu Glu Thr Ala Gln Gln Pro Val
            340                 345                 350
Met Thr Pro Cys Lys Ile Glu Pro Ser Ile Asn His Ile Leu Ser Thr
        355                 360                 365
Arg Lys Pro Gly Lys Glu Glu Gly Asp Pro Leu Gln Arg Val Gln Ser
    370                 375                 380
His Gln Gln Ala Ser Glu Glu Lys Lys Glu Lys Met Met Tyr Cys Lys
385                 390                 395                 400
Glu Lys Ile Tyr Ala Gly Val Gly Glu Phe Ser Phe Glu Glu Ile Arg
                405                 410                 415
Ala Glu Val Phe Arg Lys Lys Leu Lys Glu Gln Arg Glu Ala Glu Leu
            420                 425                 430
Leu Thr Ser Ala Glu Lys Arg Ala Glu Met Gln Lys Gln Ile Glu Glu
        435                 440                 445
Met Glu Lys Lys Leu Lys Glu Ile Gln Thr Thr Gln Gln Glu Arg Thr
    450                 455                 460
Gly Asp Gln Gln Glu Glu Thr Met Pro Thr Lys Glu Thr Thr Lys Leu
465                 470                 475                 480
Gln Ile Ala Ser Glu Ser Gln Lys Ile Pro Gly Met Thr Leu Ser Ser
                485                 490                 495
Ser Val Cys Gln Val Asn Cys Cys Ala Arg Glu Thr Ser Leu Ala Glu
            500                 505                 510
Asn Ile Trp Gln Glu Gln Pro His Ser Lys Gly Pro Ser Val Pro Phe
        515                 520                 525
Ser Ile Phe Asp Glu Phe Leu Leu Ser Glu Lys Lys Asn Lys Ser Pro
    530                 535                 540
Pro Ala Asp Pro Pro Arg Val Leu Ala Gln Arg Arg Pro Leu Ala Val
545                 550                 555                 560
Leu Lys Thr Ser Glu Ser Ile Thr Ser Asn Glu Asp Val Ser Pro Asp
```

```
                    565                 570                 575
Val Cys Asp Glu Phe Thr Gly Ile Glu Pro Leu Ser Glu Asp Ala Ile
                580                 585                 590
Ile Thr Gly Phe Arg Asn Val Thr Ile Cys Pro Asn Pro Glu Asp Thr
            595                 600                 605
Cys Asp Phe Ala Arg Ala Ala Arg Phe Val Ser Thr Pro Phe His Glu
        610                 615                 620
Ile Met Ser Leu Lys Asp Leu Pro Ser Asp Pro Glu Arg Leu Leu Pro
625                 630                 635                 640
Glu Glu Asp Leu Asp Val Lys Thr Ser Glu Asp Gln Gln Thr Ala Cys
                645                 650                 655
Gly Thr Ile Tyr Ser Gln Thr Leu Ser Ile Lys Lys Leu Ser Pro Ile
            660                 665                 670
Ile Glu Asp Ser Arg Glu Ala Thr His Ser Ser Gly Phe Ser Gly Ser
        675                 680                 685
Ser Ala Ser Val Ala Ser Thr Ser Ser Ile Lys Cys Leu Gln Ile Pro
690                 695                 700
Glu Lys Leu Glu Leu Thr Asn Glu Thr Ser Glu Asn Pro Thr Gln Ser
705                 710                 715                 720
Pro Trp Cys Ser Gln Tyr Arg Arg Gln Leu Leu Lys Ser Leu Pro Glu
                725                 730                 735
Leu Ser Ala Ser Ala Glu Leu Cys Ile Glu Asp Arg Pro Met Pro Lys
            740                 745                 750
Leu Glu Ile Glu Lys Glu Ile Glu Leu Gly Asn Glu Asp Tyr Cys Ile
        755                 760                 765
Lys Arg Glu Tyr Leu Ile Cys Glu Asp Tyr Lys Leu Phe Trp Val Ala
770                 775                 780
Pro Arg Asn Ser Ala Glu Leu Thr Val Ile Lys Val Ser Ser Gln Pro
785                 790                 795                 800
Val Pro Trp Asp Phe Tyr Ile Asn Leu Lys Leu Lys Glu Arg Leu Asn
                805                 810                 815
Glu Asp Phe Asp His Phe Cys Ser Cys Tyr Gln Tyr Gln Asp Gly Cys
            820                 825                 830
Ile Val Trp His Gln Tyr Ile Asn Cys Phe Thr Leu Gln Asp Leu Leu
        835                 840                 845
Gln His Ser Glu Tyr Ile Thr His Glu Ile Thr Val Leu Ile Ile Tyr
    850                 855                 860
Asn Leu Leu Thr Ile Val Glu Met Leu His Lys Ala Glu Ile Val His
865                 870                 875                 880
Gly Asp Leu Ser Pro Arg Cys Leu Ile Leu Arg Asn Arg Ile His Asp
                885                 890                 895
Pro Tyr Asp Cys Asn Lys Asn Gln Ala Leu Lys Ile Val Asp Phe
            900                 905                 910
Ser Tyr Ser Val Asp Leu Arg Val Gln Leu Asp Val Phe Thr Leu Ser
        915                 920                 925
Gly Phe Arg Thr Val Gln Ile Leu Glu Gly Gln Lys Ile Leu Ala Asn
    930                 935                 940
Cys Ser Ser Pro Tyr Gln Val Asp Leu Phe Gly Ile Ala Asp Leu Ala
945                 950                 955                 960
His Leu Leu Leu Phe Lys Glu His Leu Gln Val Phe Trp Asp Gly Ser
                965                 970                 975
Phe Trp Lys Leu Ser Gln Asn Ile Ser Glu Leu Lys Asp Gly Glu Leu
            980                 985                 990
```

Trp Asn Lys Phe Phe Val Arg Ile Leu Asn Ala Asn Asp Glu Ala Thr
     995                 1000                1005

Val Ser Val Leu Gly Glu Leu Ala Ala Lys Met Asn Gly Val Phe Asp
    1010                1015                1020

Thr Thr Phe Gln Ser His Leu Asn Lys Ala Leu Trp Lys Val Gly Lys
1025                1030                1035                1040

Leu Thr Ser Pro Gly Ala Leu Leu Phe Gln
                1045                1050

<210> SEQ ID NO 3
<211> LENGTH: 3401
<212> TYPE: DNA
<213> ORGANISM: Homo sapiens

<400> SEQUENCE: 3

| | | | | | |
|---|---|---|---|---|---|
| ggtggtattc | gaatcggcgg | cggcttctag | tttgcggttc | aggtttggcc | gctgccggcc |   60 |
| agcgtcctct | ggccatggac | accccggaaa | atgtccttca | gatgcttgaa | gcccacatgc |  120 |
| agagctacaa | gggcaatgac | cctcttggtg | aatgggaaag | atacatacag | tgggtagaag |  180 |
| agaattttcc | tgagaataaa | gaatacttga | taactttact | agaacattta | atgaaggaat |  240 |
| ttttagataa | gaagaaatac | cacaatgacc | caagattcat | cagttattgt | ttaaaatttg |  300 |
| ctgagtacaa | cagtgacctc | catcaatttt | ttgagtttct | gtacaaccat | gggattggaa |  360 |
| ccctgtcatc | ccctctgtac | attgcctggg | cggggcatct | ggaagcccaa | ggagagctgc |  420 |
| agcatgccag | tgctgtcctt | cagagaggaa | ttcaaaacca | ggctgaaccc | agagagttcc |  480 |
| tgcaacaaca | atacaggtta | tttcagacac | gcctcactga | acccatttg | ccagctcaag |  540 |
| ctagaacctc | agaacctctg | cataatgttc | aggttttaaa | tcaaatgata | acatcaaaat |  600 |
| caaatccagg | aaataacatg | gcctgcattt | ctaagaatca | gggttcagag | ctttctggag |  660 |
| tgatatcttc | agcttgtgat | aaagagtcaa | atatggaacg | aagagtgatc | acgatttcta |  720 |
| aatcagaata | ttctgtgcac | tcatcttttgg | catccaaagt | tgatgttgag | caggttgtta |  780 |
| tgtattgcaa | ggagaagctt | attcgtgggg | aatcagaatt | ttcctttgaa | gaattgagag |  840 |
| cccagaaata | caatcaacgg | agaaagcatg | agcaatgggt | aaatgaagac | agacattata |  900 |
| tgaaaaggaa | agaagcaaat | gcttttgaag | aacagctatt | aaaacagaaa | atggatgaac |  960 |
| ttcataagaa | gttgcatcag | gtggtggaga | catcccatga | ggatctgccc | gcttcccagg | 1020 |
| aaaggtccga | ggttaatcca | gcacgtatgg | ggccaagtgt | aggctcccag | caggaactga | 1080 |
| gagcgccatg | tcttccagta | acctatcagc | agacaccagt | gaacatggaa | agaaccccaa | 1140 |
| gagaggcacc | tcctgttgtt | cctcctttgg | caaatgctat | ttctgcagct | ttggtgtccc | 1200 |
| cagccaccag | ccagagcatt | gctcctcctg | ttcctttgaa | agcccagaca | gtaacagact | 1260 |
| ccatgtttgc | agtggccagc | aaagatgctg | gatgtgtgaa | taagagtact | catgaattca | 1320 |
| agccacagag | tggagcagag | atcaaagaag | ggtgtgaaac | acataaggtt | gccaacacaa | 1380 |
| gttcttttca | cacaactcca | aacacatcac | tgggaatggt | tcaggcaacg | ccatccaaag | 1440 |
| tgcagccatc | acccaccgtg | cacacaaaag | aagcattagg | tttcatcatg | aatatgtttc | 1500 |
| aggctcctac | acttcctgat | atttctgatg | acaaagatga | atggcaatct | ctagatcaaa | 1560 |
| atgaagatgc | atttgaagcc | cagtttcaaa | aaatgtaag | gtcatctggg | gcttggggag | 1620 |
| tcaataagat | catctcttct | ttgtcatctg | cttttcatgt | gtttgaagat | ggaaacaaag | 1680 |
| aaaattatgg | attaccacag | cctaaaaata | aacccacagg | agccaggacc | tttggagaac | 1740 |

-continued

```
gctctgtcag cagacttcct tcaaaaccaa aggaggaagt gcctcatgct gaagagtttt    1800
tggatgactc aactgtatgg ggtattcgct gcaacaaaac cctggcaccc agtcctaaga    1860
gcccaggaga cttcacatct gctgcacaac ttgcgtctac accattccac aagcttccag    1920
tggagtcagt gcacatttta aagataaag aaaatgtggt agcaaaacag tgtacccagg    1980
cgactttgga ttcttgtgag aaaacatgg tggtgccttc aagggatgga aaattcagtc    2040
caattcaaga gaaagcccca aacaggcct tgtcgtctca catgtattca gcatccttac    2100
ttcgtctgag ccagcctgct gcaggtgggg tacttacctg tgaggcagag ttgggcgttg    2160
aggcttgcag actcacagac actgacgctg ccattgcaga agatccacca ggatccgctg    2220
ccattgcaga gatccacca gatgctattg ctgggctcca agcagaatgg atgcagatga    2280
gttcacttgg gactgttgat gctccaaact tcattgttgg gaacccatgg gatgataagc    2340
tgattttcaa acttttatct gggctttcta accagtgag ttcctatcca atacttttg     2400
aatggcaatg taaacttcca gccatcaagc ccaagactga atttcaattg ggttctaagc    2460
tggtctatgt ccatcacctt cttggagaag gagcctttgc ccaggtgtac gaagctaccc    2520
agggagatct gaatgatgct aaaaataaac agaaatttgt tttaaaggtc caaaagcctg    2580
ccaacccctg ggaattctac attgggaccc agttgatgga aagactaaag ccatctatgc    2640
agcacatgtt tatgaagttc tattctgccc acttattcca gaatggcagt gtattagtag    2700
gagagctcta cagctatgga acattattaa atgccattaa cctctataaa aatacccctg    2760
aaaaagtgat gcctcaaggt cttgtcatct cttttgctat gagaatgctt tacatgattg    2820
agcaagtgca tgactgtgaa atcattcatg gagacattaa accagacaat tcatacttg     2880
gaaacggatt tttggaacag gatgatgaag atgatttatc tgctggcttg gcactgattg    2940
acctgggtca gagtatagat atgaaacttt ttccaaaagg aactatattc acagcaaagt    3000
gtgaaacatc tggttttcag tgtgttgaga tgctcagcaa caaaccatgg aactaccaga    3060
tcgattactt tggggttgct gcaacagtat attgcatgct ctttggcact tacatgaaag    3120
tgaaaaatga aggaggagag tgtaagcctg aaggtctttt tagaaggctt cctcatttgg    3180
atatgtggaa tgaattttt catgttatgt tgaatattcc agattgtcat catcttccat     3240
ctttggattt gttaaggcaa aagctgaaga agtatttca acaacactat actaacaaga    3300
ttagggccct acgtaatagg ctaattgtac tgctcttaga atgtaagcgt tcacgaaaat    3360
aaaatttgga tatagacagt ccttaaaaat caaaaaaaaa a                        3401
```

<210> SEQ ID NO 4
<211> LENGTH: 1095
<212> TYPE: PRT
<213> ORGANISM: Homo sapiens

<400> SEQUENCE: 4

```
Met Asp Thr Pro Glu Asn Val Leu Gln Met Leu Glu Ala His Met Gln
 1               5                  10                  15

Ser Tyr Lys Gly Asn Asp Pro Leu Gly Glu Trp Glu Arg Tyr Ile Gln
            20                  25                  30

Trp Val Glu Glu Asn Phe Pro Glu Asn Lys Glu Tyr Leu Ile Thr Leu
        35                  40                  45

Leu Glu His Leu Met Lys Glu Phe Leu Asp Lys Lys Tyr His Asn
    50                  55                  60

Asp Pro Arg Phe Ile Ser Tyr Cys Leu Lys Phe Ala Glu Tyr Asn Ser
65                  70                  75                  80
```

-continued

```
Asp Leu His Gln Phe Phe Glu Phe Leu Tyr Asn His Gly Ile Gly Thr
                85                  90                  95

Leu Ser Ser Pro Leu Tyr Ile Ala Trp Ala Gly His Leu Glu Ala Gln
            100                 105                 110

Gly Glu Leu Gln His Ala Ser Ala Val Leu Gln Arg Gly Ile Gln Asn
        115                 120                 125

Gln Ala Glu Pro Arg Glu Phe Leu Gln Gln Tyr Arg Leu Phe Gln
    130                 135                 140

Thr Arg Leu Thr Glu Thr His Leu Pro Ala Gln Ala Arg Thr Ser Glu
145                 150                 155                 160

Pro Leu His Asn Val Gln Val Leu Asn Gln Met Ile Thr Ser Lys Ser
                165                 170                 175

Asn Pro Gly Asn Asn Met Ala Cys Ile Ser Lys Asn Gln Gly Ser Glu
            180                 185                 190

Leu Ser Gly Val Ile Ser Ser Ala Cys Asp Lys Glu Ser Asn Met Glu
        195                 200                 205

Arg Arg Val Ile Thr Ile Ser Lys Ser Glu Tyr Ser Val His Ser Ser
    210                 215                 220

Leu Ala Ser Lys Val Asp Val Glu Gln Val Val Met Tyr Cys Lys Glu
225                 230                 235                 240

Lys Leu Ile Arg Gly Glu Ser Glu Phe Ser Phe Glu Glu Leu Arg Ala
                245                 250                 255

Gln Lys Tyr Asn Gln Arg Arg Lys His Glu Gln Trp Val Asn Glu Asp
            260                 265                 270

Arg His Tyr Met Lys Arg Lys Glu Ala Asn Ala Phe Glu Glu Gln Leu
        275                 280                 285

Leu Lys Gln Lys Met Asp Glu Leu His Lys Lys Leu His Gln Val Val
    290                 295                 300

Glu Thr Ser His Glu Asp Leu Pro Ala Ser Gln Glu Arg Ser Glu Val
305                 310                 315                 320

Asn Pro Ala Arg Met Gly Pro Ser Val Gly Ser Gln Gln Glu Leu Arg
                325                 330                 335

Ala Pro Cys Leu Pro Val Thr Tyr Gln Gln Thr Pro Val Asn Met Glu
            340                 345                 350

Lys Asn Pro Arg Glu Ala Pro Pro Val Val Pro Pro Leu Ala Asn Ala
        355                 360                 365

Ile Ser Ala Ala Leu Val Ser Pro Ala Thr Ser Gln Ser Ile Ala Pro
    370                 375                 380

Pro Val Pro Leu Lys Ala Gln Thr Val Thr Asp Ser Met Phe Ala Val
385                 390                 395                 400

Ala Ser Lys Asp Ala Gly Cys Val Asn Lys Ser Thr His Glu Phe Lys
                405                 410                 415

Pro Gln Ser Gly Ala Glu Ile Lys Glu Gly Cys Glu Thr His Lys Val
            420                 425                 430

Ala Asn Thr Ser Ser Phe His Thr Thr Pro Asn Thr Ser Leu Gly Met
        435                 440                 445

Val Gln Ala Thr Pro Ser Lys Val Gln Pro Ser Pro Thr Val His Thr
    450                 455                 460

Lys Glu Ala Leu Gly Phe Ile Met Asn Met Phe Gln Ala Pro Thr Leu
465                 470                 475                 480

Pro Asp Ile Ser Asp Asp Lys Asp Glu Trp Gln Ser Leu Asp Gln Asn
                485                 490                 495

Glu Asp Ala Phe Glu Ala Gln Phe Gln Lys Asn Val Arg Ser Ser Gly
```

-continued

```
                500                 505                 510
Ala Trp Gly Val Asn Lys Ile Ile Ser Ser Leu Ser Ser Ala Phe His
            515                 520                 525
Val Phe Glu Asp Gly Asn Lys Glu Asn Tyr Gly Leu Pro Gln Pro Lys
530                 535                 540
Asn Lys Pro Thr Gly Ala Arg Thr Phe Gly Glu Arg Ser Val Ser Arg
545                 550                 555                 560
Leu Pro Ser Lys Pro Lys Glu Val Pro His Ala Glu Glu Phe Leu
            565                 570                 575
Asp Asp Ser Thr Val Trp Gly Ile Arg Cys Asn Lys Thr Leu Ala Pro
                580                 585                 590
Ser Pro Lys Ser Pro Gly Asp Phe Thr Ser Ala Ala Gln Leu Ala Ser
            595                 600                 605
Thr Pro Phe His Lys Leu Pro Val Glu Ser Val His Ile Leu Glu Asp
            610                 615                 620
Lys Glu Asn Val Val Ala Lys Gln Cys Thr Gln Ala Thr Leu Asp Ser
625                 630                 635                 640
Cys Glu Glu Asn Met Val Val Pro Ser Arg Asp Gly Lys Phe Ser Pro
                645                 650                 655
Ile Gln Glu Lys Ser Pro Lys Gln Ala Leu Ser Ser His Met Tyr Ser
            660                 665                 670
Ala Ser Leu Leu Arg Leu Ser Gln Pro Ala Ala Gly Val Leu Thr
            675                 680                 685
Cys Glu Ala Glu Leu Gly Val Glu Ala Cys Arg Leu Thr Asp Thr Asp
        690                 695                 700
Ala Ala Ile Ala Glu Asp Pro Pro Gly Ser Ala Ala Ile Ala Glu Asp
705                 710                 715                 720
Pro Pro Asp Ala Ile Ala Gly Leu Gln Ala Glu Trp Met Gln Met Ser
                725                 730                 735
Ser Leu Gly Thr Val Asp Ala Pro Asn Phe Ile Val Gly Asn Pro Trp
            740                 745                 750
Asp Asp Lys Leu Ile Phe Lys Leu Leu Ser Gly Leu Ser Lys Pro Val
            755                 760                 765
Ser Ser Tyr Pro Asn Thr Phe Glu Trp Gln Cys Lys Leu Pro Ala Ile
770                 775                 780
Lys Pro Lys Thr Glu Phe Gln Leu Gly Ser Lys Leu Val Tyr Val His
785                 790                 795                 800
His Leu Leu Gly Glu Gly Ala Phe Ala Gln Val Tyr Glu Ala Thr Gln
                805                 810                 815
Gly Asp Leu Asn Asp Ala Lys Asn Lys Gln Lys Phe Val Leu Lys Val
            820                 825                 830
Gln Lys Pro Ala Asn Pro Trp Glu Phe Tyr Ile Gly Thr Gln Leu Met
            835                 840                 845
Glu Arg Leu Lys Pro Ser Met Gln His Met Phe Met Lys Phe Tyr Ser
850                 855                 860
Ala His Leu Phe Gln Asn Gly Ser Val Leu Val Gly Glu Leu Tyr Ser
865                 870                 875                 880
Tyr Gly Thr Leu Leu Asn Ala Ile Asn Leu Tyr Lys Asn Thr Pro Glu
                885                 890                 895
Lys Val Met Pro Gln Gly Leu Val Ile Ser Phe Ala Met Arg Met Leu
            900                 905                 910
Tyr Met Ile Glu Gln Val His Asp Cys Glu Ile Ile His Gly Asp Ile
            915                 920                 925
```

Lys Pro Asp Asn Phe Ile Leu Gly Asn Gly Phe Leu Glu Gln Asp Asp
    930                 935                 940

Glu Asp Asp Leu Ser Ala Gly Leu Ala Leu Ile Asp Leu Gly Gln Ser
945                 950                 955                 960

Ile Asp Met Lys Leu Phe Pro Lys Gly Thr Ile Phe Thr Ala Lys Cys
                965                 970                 975

Glu Thr Ser Gly Phe Gln Cys Val Glu Met Leu Ser Asn Lys Pro Trp
            980                 985                 990

Asn Tyr Gln Ile Asp Tyr Phe Gly Val Ala Ala Thr Val Tyr Cys Met
        995                 1000                1005

Leu Phe Gly Thr Tyr Met Lys Val Lys Asn Glu Gly Gly Glu Cys Lys
    1010                1015                1020

Pro Glu Gly Leu Phe Arg Arg Leu Pro His Leu Asp Met Trp Asn Glu
1025                1030                1035                1040

Phe Phe His Val Met Leu Asn Ile Pro Asp Cys His His Leu Pro Ser
                1045                1050                1055

Leu Asp Leu Leu Arg Gln Lys Leu Lys Lys Val Phe Gln Gln His Tyr
            1060                1065                1070

Thr Asn Lys Ile Arg Ala Leu Arg Asn Arg Leu Ile Val Leu Leu Leu
        1075                1080                1085

Glu Cys Lys Arg Ser Arg Lys
    1090                1095

<210> SEQ ID NO 5
<211> LENGTH: 1259
<212> TYPE: DNA
<213> ORGANISM: Homo sapiens

<400> SEQUENCE: 5
ggcacgttcg gcacgaggaa gcaaggaggc ggcggcggcc gagcgagtgg cgagtagtgg      60
aaacgttgct tctgagggga gcccaagatg accggttcta acgagttcaa gctgaaccag     120
ccacccgagg atggcatctc ctccgtgaag ttcagcccca cacctcccca gttcctgctt     180
gtctcctcct gggacacgtc cgtgcgtctc tacgatgtgc cggccaactc catgcggctc     240
aagtaccagc acaccggcgc cgtcctggac tgcgccttct acgatccaac gcatgcctgg     300
agtggaggac tagatcatca attgaaaatg catgatttga acactgatca gaaaatcttt     360
gttgggaccc atgatgcccc tatcagatgt gttgaatact gtccagaagt gaatgtgatg     420
gtcactggaa gttgggatca gacagttaaa ctgtgggatc cagaactcc ttgtaatgct      480
gggaccttct ctcagcctga aaaggtatat accctctcag tgtctggaga ccggctgatt     540
gtgggaacag caggccgcag agtgttggtg tgggacttac ggaacatggg ttacgtgcag     600
cagcgcaggg agtccagcct gaaataccag actcgctgca tacgagcgtt tccaaacaag     660
cagggttatg tattaagctc tattgaaggc cgagtggcag ttgagtattt ggacccaagc     720
cctgaggtac agaagaagaa gtatgccttc aaatgtcaca gactaaaaga aaataatatt     780
gagcagattt acccagtcaa tgccatttct tttcacaata tccacaatac atttgccaca     840
ggtggttctg atggctttgt aaatatttgg gatccattta caaaaaagcg actgtgccaa     900
ttccatcggt accccacgag catcgcatca cttgccttca gtaatgatgg gactacgctt     960
gcaatagcgt catcatatat gtatgaaatg gatgacacag aacatcctga agatggtatc    1020
ttcattcgcc aagtgacaga tgcagaaaca aaacccaagt caccatgtac ttgacaagat    1080
ttcatttact taagtgccat gttgatgata ataaaacaat tcgtactccc caatggtgga    1140

-continued

```
tttattacta ttaaagaaac cagggaaaat attaatttta atattataac aacctgaaaa    1200
taatggaaaa gaggtttttg aatttttttt tttaaataaa caccttctta agtgcaaaa    1259
```

<210> SEQ ID NO 6
<211> LENGTH: 328
<212> TYPE: PRT
<213> ORGANISM: Homo sapiens

<400> SEQUENCE: 6

```
Met Thr Gly Ser Asn Glu Phe Lys Leu Asn Gln Pro Pro Glu Asp Gly
  1               5                  10                  15

Ile Ser Ser Val Lys Phe Ser Pro Asn Thr Ser Gln Phe Leu Leu Val
             20                  25                  30

Ser Ser Trp Asp Thr Ser Val Arg Leu Tyr Asp Val Pro Ala Asn Ser
         35                  40                  45

Met Arg Leu Lys Tyr Gln His Thr Gly Ala Val Leu Asp Cys Ala Phe
 50                  55                  60

Tyr Asp Pro Thr His Ala Trp Ser Gly Gly Leu Asp His Gln Leu Lys
 65                  70                  75                  80

Met His Asp Leu Asn Thr Asp Gln Glu Asn Leu Val Gly Thr His Asp
                 85                  90                  95

Ala Pro Ile Arg Cys Val Glu Tyr Cys Pro Glu Val Asn Val Met Val
            100                 105                 110

Thr Gly Ser Trp Asp Gln Thr Val Lys Leu Trp Asp Pro Arg Thr Pro
        115                 120                 125

Cys Asn Ala Gly Thr Phe Ser Gln Pro Glu Lys Val Tyr Thr Leu Ser
130                 135                 140

Val Ser Gly Asp Arg Leu Ile Val Gly Thr Ala Gly Arg Arg Val Leu
145                 150                 155                 160

Val Trp Asp Leu Arg Asn Met Gly Tyr Val Gln Gln Arg Arg Glu Ser
                165                 170                 175

Ser Leu Lys Tyr Gln Thr Arg Cys Ile Arg Ala Phe Pro Asn Lys Gln
            180                 185                 190

Gly Tyr Val Leu Ser Ser Ile Glu Gly Arg Val Ala Val Glu Tyr Leu
        195                 200                 205

Asp Pro Ser Pro Glu Val Gln Lys Lys Tyr Ala Phe Lys Cys His
    210                 215                 220

Arg Leu Lys Glu Asn Asn Ile Glu Gln Ile Tyr Pro Val Asn Ala Ile
225                 230                 235                 240

Ser Phe His Asn Ile His Asn Thr Phe Ala Thr Gly Gly Ser Asp Gly
                245                 250                 255

Phe Val Asn Ile Trp Asp Pro Phe Asn Lys Lys Arg Leu Cys Gln Phe
            260                 265                 270

His Arg Tyr Pro Thr Ser Ile Ala Ser Leu Ala Phe Ser Asn Asp Gly
        275                 280                 285

Thr Thr Leu Ala Ile Ala Ser Ser Tyr Met Tyr Glu Met Asp Asp Thr
    290                 295                 300

Glu His Pro Glu Asp Gly Ile Phe Ile Arg Gln Val Thr Asp Ala Glu
305                 310                 315                 320

Thr Lys Pro Lys Ser Pro Cys Thr
                325
```

<210> SEQ ID NO 7
<211> LENGTH: 25

-continued

```
<212> TYPE: DNA
<213> ORGANISM: Homo sapiens

<400> SEQUENCE: 7
gctgatcacc tgttctttct tgctc                                                25

<210> SEQ ID NO 8
<211> LENGTH: 28
<212> TYPE: DNA
<213> ORGANISM: Homo sapiens

<400> SEQUENCE: 8
atcgtcgact ccaccattgg ggagtacg                                             28

<210> SEQ ID NO 9
<211> LENGTH: 29
<212> TYPE: DNA
<213> ORGANISM: Homo sapiens

<400> SEQUENCE: 9
cgggatccag gtccaaaagc ctgccaacc                                            29

<210> SEQ ID NO 10
<211> LENGTH: 27
<212> TYPE: DNA
<213> ORGANISM: Homo sapiens

<400> SEQUENCE: 10
cgggatcctg ctgggagcct acacttg                                              27

<210> SEQ ID NO 11
<211> LENGTH: 29
<212> TYPE: DNA
<213> ORGANISM: Homo sapiens

<400> SEQUENCE: 11
cgggatccaa gcctcaacgc ccaactctg                                            29

<210> SEQ ID NO 12
<211> LENGTH: 18
<212> TYPE: DNA
<213> ORGANISM: Homo sapiens

<400> SEQUENCE: 12
ctgagtggag atgcctcc                                                        18

<210> SEQ ID NO 13
<211> LENGTH: 20
<212> TYPE: DNA
<213> ORGANISM: Homo sapiens

<400> SEQUENCE: 13
ctggcaaggt agacaagccg                                                      20
```